US011461690B2

(12) United States Patent
Szeto et al.

(10) Patent No.: US 11,461,690 B2
(45) Date of Patent: Oct. 4, 2022

(54) DISTRIBUTED MACHINE LEARNING SYSTEMS, APPARATUS, AND METHODS

(71) Applicants: Nant Holdings IP, LLC, Culver City, CA (US); NantOmics, LLC, Culver City, CA (US)

(72) Inventors: Christopher Szeto, Scotts Valley, CA (US); Stephen Charles Benz, Santa Cruz, CA (US); Nicholas J. Witchey, Laguna Hills, CA (US)

(73) Assignees: NANTOMICS, LLC, Culver City, CA (US); NANT HOLDINGS IP, LLC, Culver City, CA (US)

( * ) Notice: Subject to any disclaimer, the term of this patent is extended or adjusted under 35 U.S.C. 154(b) by 233 days.

(21) Appl. No.: 15/651,345

(22) Filed: Jul. 17, 2017

(65) Prior Publication Data

US 2018/0018590 A1 Jan. 18, 2018

Related U.S. Application Data

(60) Provisional application No. 62/363,697, filed on Jul. 18, 2016.

(51) Int. Cl.
*G06N 20/00* (2019.01)
*G06N 20/10* (2019.01)
(Continued)

(52) U.S. Cl.
CPC ......... *G06N 20/00* (2019.01); *G06F 21/6254* (2013.01); *G06N 20/10* (2019.01);
(Continued)

(58) Field of Classification Search
CPC ..... G06N 20/00; G06F 21/6254; G16H 40/20
See application file for complete search history.

(56) References Cited

U.S. PATENT DOCUMENTS 7,899,225 B2  3/2011 Collins et al.
7,974,714 B2  7/2011 Hoffberg
(Continued)

FOREIGN PATENT DOCUMENTS

CA    2795554 A1   10/2011
CN  102413872 A    4/2012
(Continued)

OTHER PUBLICATIONS

Mitra et al., "Eigen-Profiles of Spatio-Temporal Fragments for Adaptive Region-Based Tracking," pp. 1497-1500 (IEEE 2012) (Year: 2012).*

(Continued)

*Primary Examiner* — Brian M Smith
*Assistant Examiner* — Kevin L. Smith
(74) *Attorney, Agent, or Firm* — Harness Dickey & Pierce P.L.C.

(57) ABSTRACT

A distributed, online machine learning system is presented. Contemplated systems include many private data servers, each having local private data. Researchers can request that relevant private data servers train implementations of machine learning algorithms on their local private data without requiring de-identification of the private data or without exposing the private data to unauthorized computing systems. The private data servers also generate synthetic or proxy data according to the data distributions of the actual data. The servers then use the proxy data to train proxy models. When the proxy models are sufficiently similar to the trained actual models, the proxy data, proxy model parameters, or other learned knowledge can be transmitted to one or more non-private computing devices. The learned knowledge from many private data servers can then be aggregated into one or more trained global models without exposing private data.

35 Claims, 6 Drawing Sheets

(51) Int. Cl.
  *G16H 50/50* (2018.01)
  *G16H 50/20* (2018.01)
  *G16H 10/60* (2018.01)
  *G16H 40/20* (2018.01)
  *G06F 21/62* (2013.01)

(52) U.S. Cl.
  CPC ............. *G16H 10/60* (2018.01); *G16H 40/20* (2018.01); *G16H 50/20* (2018.01); *G16H 50/50* (2018.01); *G06F 21/6245* (2013.01)

(56) References Cited

U.S. PATENT DOCUMENTS

| | | | |
|---|---|---|---|
| 8,755,837 | B2 | 6/2014 | Rhoads et al. |
| 8,873,813 | B2 | 10/2014 | Tadayon et al. |
| 8,954,365 | B2 | 2/2015 | Criminisi et al. |
| 9,202,253 | B2 | 12/2015 | Macoviak et al. |
| 9,224,180 | B2 | 12/2015 | Macoviak et al. |
| 9,646,134 | B2 | 5/2017 | Sanborn et al. |
| 2005/0197783 | A1 | 9/2005 | Kuchinsky et al. |
| 2006/0063156 | A1 | 3/2006 | Willman et al. |
| 2009/0037351 | A1* | 2/2009 | Kristal ............... G06Q 10/04 706/12 |
| 2009/0203588 | A1 | 8/2009 | Willman et al. |
| 2010/0168533 | A1 | 7/2010 | Johnsen et al. |
| 2011/0179011 | A1* | 7/2011 | Cardno ............. G06F 21/6227 707/709 |
| 2011/0228976 | A1 | 9/2011 | Fitzgibbon et al. |
| 2012/0288186 | A1* | 11/2012 | Kohli ................ G06K 9/6255 382/159 |
| 2012/0303558 | A1 | 11/2012 | Jaiswal |
| 2013/0085773 | A1* | 4/2013 | Yao .................... G06Q 10/04 705/2 |
| 2013/0090254 | A1 | 4/2013 | Lamb et al. |
| 2014/0038836 | A1 | 2/2014 | Higgins et al. |
| 2014/0046696 | A1 | 2/2014 | Higgins et al. |
| 2014/0074760 | A1 | 3/2014 | Boldyrev et al. |
| 2014/0088989 | A1 | 3/2014 | Krishnapuram et al. |
| 2014/0201126 | A1 | 7/2014 | Zadeh et al. |
| 2014/0222349 | A1 | 8/2014 | Higgins et al. |
| 2014/0222737 | A1* | 8/2014 | Chen .................. G06N 20/20 706/12 |
| 2014/0343955 | A1* | 11/2014 | Raman ............... G16H 50/20 705/2 |
| 2015/0120329 | A1* | 4/2015 | Rangadass ......... G06F 19/321 705/3 |
| 2015/0154646 | A1* | 6/2015 | Mishra ............... G06Q 50/24 705/3 |
| 2015/0170055 | A1 | 6/2015 | Beymer et al. |
| 2015/0199010 | A1 | 7/2015 | Coleman et al. |
| 2016/0055307 | A1 | 2/2016 | Macoviak et al. |
| 2016/0055410 | A1 | 2/2016 | Spagnola |
| 2016/0055427 | A1 | 2/2016 | Adjaoute |
| 2016/0071017 | A1 | 3/2016 | Adjaoute |
| 2016/0078367 | A1 | 3/2016 | Adjaoute |
| 2016/0260023 | A1* | 9/2016 | Miserendino, Jr. .... G06N 20/00 |

FOREIGN PATENT DOCUMENTS

| | | | |
|---|---|---|---|
| DE | 102005020618 | A1 | 12/2005 |
| EP | 17831625 | * | 11/2020 |
| JP | 2013523154 | A | 6/2013 |
| WO | WO-2010126624 | A1 | 11/2010 |
| WO | WO-2010126625 | A1 | 11/2010 |
| WO | WO-2011127150 | A2 | 10/2011 |
| WO | WO-2015149035 | A1 | 10/2015 |

OTHER PUBLICATIONS

Poh et al., "Challenges in Designing an Online Healthcare Platform for Personalised Patient Analytics," pp. 1-6 (IEEE 2014) (Year: 2014).*
Emre Kiciman, "Using Statistical Monitoring to Detect Failures in Internet Services," Stanford University Dissertation (2005) (Year: 2005).*
Parks et al., "Perturbed Gibbs Samplers for Generating Large-Scale Privacy-Safe Synthetic Health Data," IEEE (2013) (Year: 2013).*
Securosis, "Understanding and Selecting Data Masking Solutions: Creating Secure and Useful Data," (Aug. 10, 2012) (Year: 2012).*
Mikolov et al., "Distributed Representations of Words and Phrases and their Compositionality," NIPS (2013) (Year: 2013).*
Nicolas P. Terry, "Big Data Proxies and Health Privacy Exceptionalism," 24 Health Matrix (2014) (Year: 2014).*
Stojanovic et al., "Modeling Healthcare Quality via Compact Representations of Electronic Health Records," Computational Biology & Bioinfomatics (IEEE May 2016) (Year: 2016).*
Definition of "Salient," Oxford English Dictionary (WayBack Machine, Jun. 2016) (Year: 2016).*
OneLook Online Thesaurus at <https://onelook.com/thesaurus/?s=transmit>, retrieved 2021 (Year: 2021).*
He et al., "CRFs based de-identification of medical records," (2015) (Year: 2015).*
Supplementary European Search Report, EP 12835860 to Yao et al. (dated 2015) (Year: 2015).*
Luo et al., "A distributed approach to enabling privacy-preserving model-based classifier training," Knowledge Information Systems (2009) (Year: 2009).*
Khatri et al., "Architecture for Preserving Privacy During Data Mining by Hybridization of Partitioning on Medical Data," IEEE 2010 (Year: 2010).*
International Search Report and Written Opinion in counterpad International Application No. PCT/US17/42356, dated Sep. 26, 2017 (9 pages).
Bareinboim, Elias et al.; Casual Inference and the Data-Fusion Problem; CrossMark Colloquium Paper; Jun. 29, 2015; 8 pages.
Daemen, Anneleen et al.; Development of a Kernel Function for Clinical Data; 31st Annual International Conference of the IEEE EMBS; Sep. 2009; 5 pages.
International Search Report and Written Opinion for PCT Application No. PCT/US17/42356; dated Sep. 26, 2017; 8 pages.
International Preliminary Report on Patentability for PCT Application No. PCT/US17/42356; dated Sep. 26, 2017; 7 pages.
Patki et al.; The Synthetic data vault; Oct. 17, 2016; 12 pages.
Koperniak; Artificial data give the same results as real data - without compromising privacy; Mar. 6, 2017; 3 pages.
Feldman et al.; Dimensionality Reduction of Massive Sparse Datasets Using Coresets; Mar. 5, 2015; 11 pages.
Hardesty; Big data technique shrinks data sets while preserving their fundamental mathematical relationships; Dec. 15, 2016; 5 pages.
Knight; How AI could save lives without spilling medical secrets; May 14, 2019; 3 pages.
McMahan et al.; Federated Learning: Collaborative Machine Learning without Centralized Training Data; Google AI Blog; Apr. 6, 2017.
Huang et al.; Patient Clustering Improves Efficiency of Federated Machine Learning to Predict Mortality and Hospital Stay Time using Distributed Electronic Medical Records; Mar. 22, 2019; 21 pages.
Wiggers; Federated Learning Technique Predicts Hospital Stay and Patient Mortality; Mar. 25, 2019; 2 pages.
Office Action for Canadian Application No. 3,031,067; dated Jan. 6, 2020; 7 pages.
Office Action for Japanese Application No. 2019-502045; dates Mar. 10, 2020; 2 pages.
Office Action for Japanese Application No. 2019-502045; dated Jun. 17, 2020; 2 pages.

* cited by examiner

DISTRIBUTED MACHINE LEARNING SYSTEMS, APPARATUS, AND METHODS

CROSS REFERENCE TO RELATED APPLICATION

This application claims the priority under 35 USC 119 from U.S. Provisional Patent Application Ser. 62/363,697, entitled Distributed Machine Learning Systems, Apparatus, and Methods, filed on Jul. 18, 2016 by Szeto, the contents of which are incorporated by reference in their entirety.

FIELD OF THE INVENTION

The field of the invention is distributed machine learning technologies.

BACKGROUND

The background description includes information that may be useful in understanding the present inventive subject matter. It is not an admission that any of the information provided herein is prior art or relevant to the presently claimed inventive subject matter, or that any publication specifically or implicitly referenced is prior art.

With the recent growth of highly accessible and cost-effective machine learning platforms (e.g., Google®'s Artificial Intelligence including TensorFlow, Amazon's Machine Learning, Microsoft's Azure Machine Learning, OpenAI, SciKit-Learn, Matlab, etc.), data analysts have numerous off-the-shelf options available to them for conducting automated analysis of large data sets. Additionally, in parallel to the growth of machine learning platforms, target data sets have also grown in size. For example, Yahoo! has released several large data sets to the public having sizes on the order of terabytes and The Cancer Genome Atlas (TCGA) data portal offers access to massive amounts of clinical information and genomic characterization data. These pre-built data sets are made readily available to data analysts.

Unfortunately, researchers often encounter obstacles when compiling data sets for their in-progress research, especially when attempting to build trained machine learning models capable of generating interesting predictions using in-the-field data. One major obstacle is that researchers often lack access to the data they require. Consider, for example, a scenario where a researcher wishes to build a trained model from patient data where the patient data is stored in multiple hospitals' electronic medical record databases. The researcher would likely not have authorization to access each hospital's patient data due to privacy restrictions or HIPAA compliance. In order to compile a desired data set, the researcher must request the data from the hospital. Assuming the hospital is amenable to the request, the hospital must then de-identify the data to remove references to specific patients before providing the data to the researcher. However, de-identification results in loss of possibly valuable information in the dataset that could be instrumental in training machine learning algorithms, which in turn can provide opportunities for discovering new relationships in the data or provide value predictive properties. Thus, because of the security restrictions, the datasets available to the researcher could lack information. Clearly, researchers would benefit from technologies that could extract learned information or "knowledge" while also respecting private or secured information distributed across multiple data stores.

Interestingly, previous efforts associated with analyzing distributed data focus on the nature of machine learning rather than dealing with the technical issues of isolated, private data. For example, U.S. Pat. No. 7,899,225 to Collins et al. titled "Systems and Methods of Clinical State Prediction Utilizing Medical Image Data" filed Oct. 26, 2006, describes creating and merging statistical models to create a final multi-dimensional classification space. The statistical models are the mathematical variation models which define the space in which subjects can be represented. Unfortunately, Collins assumes that the system has authorization to access all the data in order to build the predictive models. Collins also fails to provide insights into circumstances where non-centralized data must remain secure or private. Still, it would be useful to be able to combine trained models in some way.

Consider U.S. Pat. No. 8,954,365 to Criminisi et al. titled "Density Estimation and/or Manifold Learning", filed Jun. 21, 2012. Rather than focusing on methods of combining models, Criminisi focuses on simplifying a data set. Criminisi describes a dimensional reduction technique that maps unlabeled data to a lower dimensional space whilst preserving relative distances or other relationships among the unlabeled data points. While useful in reducing computational efforts, such techniques fail to address how to combine models that depend on disparate, private data sets.

Yet another example that attempts to address de-identification of data includes U.S. patent application publication 2014/0222349 to Higgins et al. titled "System and Methods for Pharmacogenomic Classification" filed Jan. 15, 2014. Higgins describes using surrogate phenotypes that represent clusters in pharmacogenomics populations within de-identified absorption, distribution, metabolism, and excretion (ADME) drug data. The surrogate phonotypes are then used to train learning machines (e.g., a support vector machine) that can then be used for classification of live patient data. Although Higgins provides for building trained learning machines based on surrogate phenotypes, Higgins requires access to de-identified data to build the initial training set. As mentioned previously, de-identified data robs a training dataset of some of its value.

In distributed environments where there can be many entities housing private data, it is not possible to ensure access to large amounts of high quality, de-identified data. This is especially true when a new learning task is launched and no data yet exists that can service the new task. Thus, there remains a considerable need for learning systems that are able to aggregate learned information or knowledge from private data sets in a distributed environment without requiring de-identification of the data before training begins.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

In some embodiments, the numbers expressing quantities of ingredients, properties such as concentration, reaction conditions, and so forth, used to describe and claim certain embodiments of the inventive subject matter are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the inventive subject matter are approximations, the numerical values set forth in the specific examples are reported as precisely as practicable. The numerical values presented in some embodiments of the inventive subject matter may contain certain errors necessarily resulting from the standard deviation found in their respective testing measurements.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the inventive subject matter and does not pose a limitation on the scope of the inventive subject matter otherwise claimed. No language in the specification should be construed as indicating any non-claimed element essential to the practice of the inventive subject matter.

Groupings of alternative elements or embodiments of the inventive subject matter disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

SUMMARY

The inventive subject matter provides apparatus, systems, and methods in which distributed, on-line machine learning computers are able to learn information or gain knowledge from private data and distribute the knowledge among peers lacking access to the private data, wherein the distributed knowledge does not include the actual private or restricted features of the local, private data.

For the purposes of this application, it is understood that the term "machine learning" refers to artificial intelligence systems configured to learn from data without being explicitly programmed. Such systems are understood to be necessarily rooted in computer technology, and in fact, cannot be implemented or even exist in the absence of computing technology. While machine learning systems utilize various types of statistical analyses, machine learning systems are distinguished from statistical analyses by virtue of the ability to learn without explicit programming and being rooted in computer technology. Thus, the present techniques utilize a distributed data structure that preserves privacy rights while also retaining learnability. Protocols that exchange compressed/learned data, as opposed to raw data, reduces bandwidth overhead.

One aspect of the inventive subject matter includes a distributed machine learning system. In some embodiments, the distributed machine learning system has a plurality of private data servers, possibly operating as peers in a distributed computing environment. Each private data server has access to its own local, private data. The other servers or peers in the system typically lack permission, authority, privilege, or access to others local, private data. Further, each private data server is communicatively coupled with one or more non-private computing devices comprising a global modeling engine; a centralized machine learning computer farm or a different private data server for example. The private data servers are computing devices having one or more processors that are configurable to execute software instructions stored in a non-transitory computer readable memory, where execution of the software instructions gives rise to a modeling engine on the private data server. The modeling engine is configurable to generate one or more trained machine learning models based on the local private data. More specifically, the modeling engine is able to receive model instructions from one or more remote computing devices over a network. The model instructions can be considered as one or more command that instruct the modeling engine to use at least some of the local private data in order to create a trained actual model according to an implementation of a machine learning algorithm (e.g., support vector machine, neural network, decision tree, random forest, deep learning neural network, etc.). The modeling engine creates the trained actual model as a function of the local private data (i.e., a selected or filtered training data set) after any required preprocessing requirements, if any, have been met (e.g., filtering, validating, normalizing, etc.). Once trained, the trained actual model will have one or more actual model parameters or metrics that describe the nature of the trained actual model (e.g., accuracy, accuracy gain, sensitivity, sensitivity gain, performance metrics, weights, learning rate, epochs, kernels, number of nodes, number of layers, etc.). The modeling engine further generates one or more private data distributions from the local private data training set where the private data distributions represent the nature of the local private data used to create the trained model. The modeling engine uses the private data distributions to generate a set of proxy data, which can be considered synthetic data or Monte Carlo data having the same general data distribution characteristics as the local private data, while also lacking the actual private or restricted features of the local, private data. In some cases, Monte Carlo simulations generate deterministic sets of proxy data, by using a seed for a pseudo random number generator. A source for truly random seeds includes those provided by random.org (see URL www.random.org). Private or restricted features of the local private data include, but are not limited to, social security numbers, patient names, addresses or any other personally identifying information, especially information protected under the HIPAA Act. The modeling engine then attempts to validate that the set of proxy data is a reasonable training set stand-in for the local, private data by creating a trained proxy model from the set of proxy data. The resulting trained proxy model is described by one or more proxy model parameters defined according to the same attribute space as the actual model parameters. The modeling engine calculates a similarity score that indicates how similar the trained actual model and the proxy model are to each other as a function of the proxy model parameters and the actual model parameters. Based on the similarity score, the modeling engine can transmit one or more pieces of information related to the trained model, possibly including the set of proxy data or information sufficient to recreate the proxy data, actual model parameters, proxy model parameters, or other features. For example, if the model similarity satisfies a similarity requirement (e.g., compared to a threshold value, etc.), the modeling engine can transmit the set of proxy data to a non-private computing device, which in turn integrates the proxy data in to an aggregated model.

Another aspect of the inventive subject matter includes computer implemented methods of distributed machine learning that respect private data. One embodiment of a method includes a private data server receiving model instructions to create a trained actual model based on at least some local, private data. The model instructions, for example, can include a request to build the trained actual model from an implementation of a machine learning algorithm. A machine learning engine, possibly executing on the private data server, continues by creating the trained actual model according to the model instructions by training the implementation of the machine learning algorithm(s) on relevant local, private data. The resulting trained model comprises one or more actual model parameters that describe the nature of the trained model. Another step of the method includes generating one or more private data distributions that describe the nature of the relevant local, private data. For example, the private data distributions could be represented by a Gaussian distribution, a Poisson distribution, a histogram, a probability distribution, or another type of distribution. From the private data distributions, the machine learning engine can identify or otherwise calculate one or more salient private data features that describe the nature of the private data distributions. Depending upon the type of distribution, example features could include sample data, a mean, a mode, an average, a width, a half-life, a slope, a moment, a histogram, higher order moments, or other types of features. In some, more specific embodiments, the salient private data features could include proxy data. Once the salient features are available, the machine learning engine transmits the salient private data features over a network to a non-private computing device; a central server or global modeling engine, for example, that can integrate the salient private data features with other data sets to create an aggregated model. Thus, multiple private peers are able to share their learned knowledge without exposing their private data.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
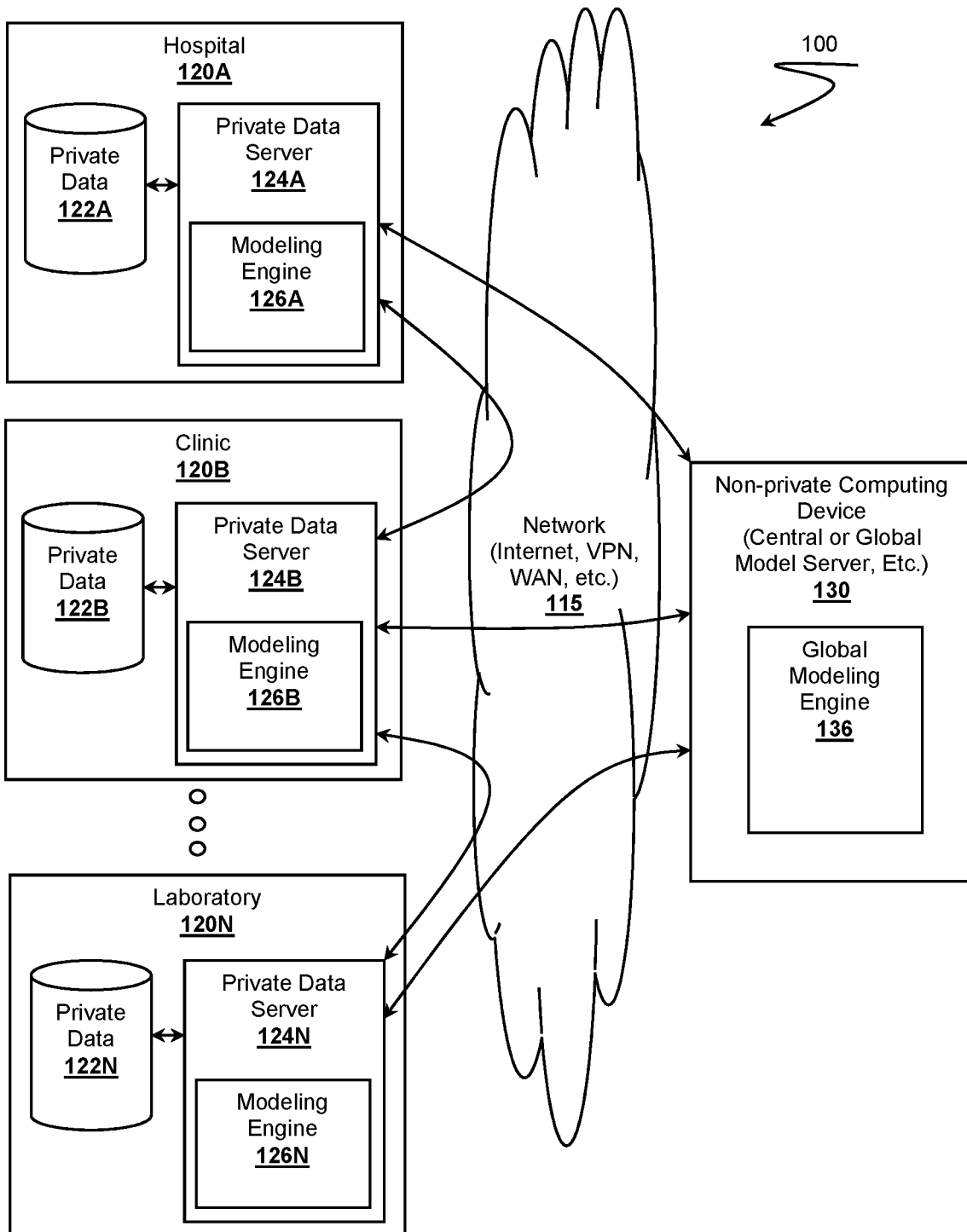
FIG. 1 is an illustration of an example distributed, online machine learning system, according to the embodiments presented herein.

It should be noted that any language directed to a computer or computing device should be read to include any suitable combination of computing devices, including servers, interfaces, systems, appliances, databases, agents, peers, engines, controllers, modules, or other types of computing devices operating individually, collectively, or cooperatively. One of ordinary skill in the art should appreciate that the computing devices comprise one or more processors configured to execute software instructions that are stored on a tangible, non-transitory computer readable storage medium (e.g., hard drive, FPGA, PLA, PLD, solid state drive, RAM, flash, ROM, external drive, memory stick, etc.). The software instructions specifically configure or program the computing device to provide the roles, responsibilities, or other functionality as discussed below with respect to the disclosed apparatus. Further, the disclosed technologies can be embodied as a computer program product that includes a tangible, non-transitory computer readable medium storing the software instructions executable by a processor to perform the disclosed steps or operations associated with implementations of computer-based algorithms, processes, methods, or other instructions. In some embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges among devices can be conducted over a packet-switched network, the Internet, LAN, WAN, VPN, or other type of packet switched network; a circuit switched network; cell switched network; or other type of network.

As used in the description herein and throughout the claims that follow, when a system, engine, server, device, module, or other computing element is described as configured to perform or execute functions on data in a memory, the meaning of "configured to" or "programmed to" is defined as one or more processors or cores of the computing element being programmed by a set of software instructions stored in the memory of the computing element to execute the set of functions on target data or data objects stored in the memory.

One should appreciate that the disclosed techniques provide many advantageous technical effects including construction of communication channels among computing devices over a network to exchange machine learning data while respecting data privacy of the underlying raw data. The computing devices are able to exchange "learned" information or knowledge among each other without comprising privacy. More specifically, rather than transmitting private or secured data to remote computing devices, the disclosed private data servers attempt to "learn" information automatically about the local private data via computer-based implementations of one or more machine learning algorithms. The learned information is then exchanged with other computers lacking authorization to access the private data. Further, it should be appreciated that the technical effects include computationally building trained proxy models from distributed, private data and their corresponding data distributions.

The focus of the disclosed inventive subject matter is to enable construction or configuration of a computing device to operate on vast quantities of digital data, beyond the capabilities of a human. Although the digital data typically represents various aspects of patient data, it should be appreciated that the digital data is a representation of one or more digital models of the patients, not "the patient" itself. By instantiation of such digital models in the memory of the computing devices, the computing devices are able to manage the digital data or models in a manner that provides utility to a user of the computing device that the user would lack without such a tool, especially within a distributed, online machine learning system. Therefore, the inventive subject matter improves or otherwise optimizes distributed machine learning in environments where the computing devices lack access to private data.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

The following discussion is presented from a health care perspective, and more specifically with respect to building trained machine learning models from genomic sequence data associated with cancer patients. However, it is fully contemplated that the architecture described herein can be adapted to other forms of research beyond oncology and can be leveraged wherever raw data is secured or considered private; insurance data, financial data, social media profile data, human capital data, proprietary experimental data, gaming or gambling data, military data, network traffic data, shopping or marketing data, or other types of data for example.

For example, the techniques presented herein can be used as part of a "learning as a service" business model. In this type of model, the organization having private data (e.g., healthcare data, genomic data, enterprise data, etc.) may generate machine learning models (e.g., trained actual models, trained proxy models, etc.) and other learned information, and may allow other groups (e.g., start-ups, other institutions, other businesses, etc.) to use these models to analyze their own data or study local data upon payment of a fee. For instance, in a healthcare setting, data collected from patients at particular healthcare institutions could be analyzed to create trained actual models and/or trained proxy models using machine learning. Researchers, data analysts, or other entrepreneurs at a different healthcare institution or company could pay a fee (e.g., one time fee, subscription, etc.) to access the models, e.g., to analyze their own data or to study local data. Thus, in this example, a machine learning model is generated based upon internal data relative to system 100, and can be used to classify external data relative to system 100.

In still other embodiments, the organization providing machine learning services could receive fees for analyzing data provided by a $3^{rd}$ party. Here, researchers, data analysts, or other entrepreneurs at different healthcare institutions could pay a fee to provide data, similar to the local private data and in a form that could be analyzed separately or could be combined with the local private data, to generate a machine learning model (e.g., a trained actual model or a trained proxy model) along with other learned information that can be used to analyze subsequent sets of data provided by the $3^{rd}$ Party. Thus, in this example, a machine learning model is generated based upon external data relative to system 100, and can be used to classify additional external data relative to system 100.

Other industries in which these types of "learning as a service" models could be employed include but are not limited to game data, military data, network traffic/security data, software execution data, simulation data, etc.

Machine learning algorithms create models that form conclusions based upon observed data. For supervised learning, a training dataset is fed into a machine learning algorithm. Here, by providing inputs and known outputs as training data, a machine learning system can create a model based upon this training data. Thus the machine learning algorithm generates a mapping function that maps inputs to an output.

In other embodiments, for unsupervised learning, a dataset is fed into a machine learning system, and the machine learning system analyses the data based upon clustering of data points. In this type of analysis, the underlying structure or distribution of the data is used to generate a model reflecting the distribution or structure of the data. This type of analysis is frequently used to detect similarities (e.g., are two images the same), identify anomalies/outliers, or to detect patterns in a set of data.

Semi-supervised models, a hybrid of the previous two approaches, utilize both supervised and unsupervised models to analyze data.

Machine learning models predict an output (e.g., using classification or regression) based upon inputs (without a known output or answer). Prediction may involve mapping inputs into a category (e.g., analyzing an image to determine whether a characteristic of the image is present). In this type of analysis, the output variable takes the form of a class label, identifying group membership. Thus, this approach can be used to select a category (e.g., based on whether an image contains a specified characteristic).

Regression analysis seeks to minimize error between a regression line and the data points used to generate the line. Here, the output variable take the form of a continuous variable (e.g., a line) to predict a continuous response. Thus, regression can be used to analyze numerical data. These techniques are described more fully below. It should be appreciated that regression analysis can occur in one or more dimensions of relevance according to the research task's requirements.

FIG. 1 is an illustration of an example distributed machine learning system 100. System 100 is configured as a computer-based research tool allowing multiple researchers or data analysts to create trained machine learning models from many private or secured data sources, to which the researchers would not normally have permission or authority to access. In the example shown, a researcher has permission to access a central machine learning hub represented as non-private computing device 130, possibly executing as a global modeling engine 136. Non-private computing device 130 can comprise one or more global model servers (e.g., cloud, SaaS, PaaS, IaaS, LaaS, farm, etc.) that offer distributed machine learning services to the researcher. However, data of interest to the researcher resides on one or more of private data servers 124A, 124B, through 124N (collectively referred to as private data servers 124) located at one or more entities 120A through 120N over network 115 (e.g., wireless network, an intranet, a cellular network, a packet switched network, an ad-hoc network, the Internet, WAN, VPN, LAN, P2P, etc.). Network 115 can include any combination of the aforementioned networks. The entities can include hospital 120A, clinic 120B, through laboratory 120N (collectively referred to as entities 120). Each of entity 120 has access to its own local private data 122A through 122N (collectively referred to as private data 122), possibly stored on a local storage facility (e.g., a RAID system, a file server, a NAS, a SAN, a network accessible storage device, a storage area network device, a local computer readable memory, a hard disk drive, an optical storage device, a tape drive, a tape library, a solid state disk, etc.). Further, each private data server 124 could include one or more of a BAM server, a SAM server, a GAR server, a BAMBAM server, or even a clinical operating system server. Each of private data server 124 has access to its own local private data 122 and has at least one of modeling engine 126. For the sake of discussion, each of private data server 120 is considered communicatively coupled, via network 115, to non-private computing device 130.

Each set of private data 122 is considered private to its corresponding entity 120. Under this consideration it should be appreciated that the other entities 120 as well as the researcher accessing the modeling services offered by non-private computing device 130 do not have rights, permissions, or other authorization to access another's private data 122. For further clarity, the term "private" and "non-private" are relative terms describing the relationship among the various pairs of entities and their corresponding data sets. For example, private data server 124B in clinic 120B has access to its local private data 122B, but does not have access to another's private data, e.g., private data 122N in laboratory 120N or private data 122A in hospital 120A. In other embodiments, private data server 124N could be considered as a non-private computing device 130 relative to the other entities. Such a consideration is especially important in embodiments where the various private servers 124 are able to communicate with each other directly over network 115, possibly in a peer-to-peer fashion or via an affiliation, rather than through a central hub. For example, if a medical institute has multiple locations and/or affiliations, e.g., a main hospital, physician offices, clinics, a secondary hospital, a hospital affiliation, each of these entities could have their own private data 122, private data server 124 and modeling engine 126, which may all be visible to each other, but not to a different entity.

Given the nature of the system and the requirements that each of entity 120 must keep its private data 122 secured, the researcher is hard pressed to gain access to the large quantities of high quality data necessary to build desirable trained machine learning models. More specifically, the researcher would have to gain authorization from each entity 120 having private data 122 that is of interest. Further, due to various restrictions (e.g., privacy policies, regulations, HIPAA compliance, etc.), each entity 120 might not be permitted to provide requested data to the researcher. Even under the assumption that the researcher is able to obtain permission from all of entities 120 to obtain their relevant private data 122, entities 120 would still have to de-identify the data sets. Such de-identification can be problematic due to the time required to de-identify the data and due to loss of information, which can impact the researcher's ability to gain knowledge from training machine learning models.

In the ecosystem/system presented in FIG. 1, the issues associated with privacy restrictions of private data 122 are addressed by focusing on the knowledge gained from a trained machine learning algorithm rather than the raw data itself. Rather than requesting raw data from each of entity 120, the researcher is able to define a desired machine learning model that he/she wishes to create. The researcher may interface with system 100 through the non-private computing device 130; through one of the private data servers 124, provided that the researcher has been granted access to the private data server; or through a device external to system 100 that can interface with non-private computing device 130. The programmatic model instructions on how to create the desired model are then submitted to each relevant private data server 124, which also has a corresponding modeling engine 126 (i.e., 126A through 126N). Each local modeling engine 126 accesses its own local private data 122 and creates local trained models according to model instructions created by the researcher. As each modeling engine 126 gains new learned information, the new knowledge is transmitted back to the researcher at non-private computing device 130 once transmission criteria have been met. The new knowledge can then be aggregated into a trained global model via global modeling engine 136. Examples of knowledge include (see, e.g., FIG. 2) but are not limited to proxy data 260, trained actual models 240, trained proxy models 270, proxy model parameters, model similarity scores, or other types of data that have been de-identified. In some embodiments, the global model server 130 analyzes sets of proxy related information (including for example proxy data 260, proxy data distributions 362, proxy model parameters 475, other proxy related data combined with seeds, etc.) to determine whether the proxy related information from one of private data server 124 has the same shape and/or overall properties as the proxy related data from another private data server 124, prior to combining such information. Proxy related information that is dissimilar may be flagged for manual review to determine whether the underlying private data distribution set is corrupted, has missing data, or contains a substantial number of outliers. In some embodiments, private patient data considered to be outliers are disregarded and excluded from the techniques disclosed herein. For example, a one-class support vector machine (SVM) could be used to identify outliers that might not be consistent with the core, relevant data. In some embodiments, the one-class SVM is constructed by external peers (e.g., non-private computing device 130, etc.) based on similar data of interest. The one-class SVM can then transmitted to the private data server 124. Private data sever 124 can then use the externally generated one-class SVM to ensure that the local data of interest is indeed consistent with external data of interest.

Thus, proxy data may be considered as a transformation of raw data into data of a different form that retains the characteristics of the raw data.

New private data 122 is accessible to private data server 124 on an ongoing basis, e.g., as test results become available, as new diagnoses are made, as new patients are added to the system, etc. For relatively small data sets, proxy data 260 or other proxy related information can be regenerated using all or nearly all of the stored private data. For larger data sets, proxy data can be regenerated using only newly added data. New data may be identified through timestamps, location of storage, geostamping, blockchain hashes, etc.

In other embodiments, new private data is incorporated in real time or in near real time into the machine learning system. Thus, as soon as new private data is available, it can be incorporated into the trained actual models and the trained proxy models. In some embodiments, the machine learning models are updated constantly, e.g., using all available private data (old and newly added private data) or only on newly added private data. Additionally, there is no set timeframe that governs machine learning model updates, and thus, certain machine learning models are updated daily, while other models are updated yearly or even on longer timeframes. This flexibility stands in contrast to traditional machine leaning models which rely on bulk processing of all of the data followed by cycles of training and testing.

In some embodiments, each private data server 124 receives the same programmatic model instructions 230 on how to create a desired model. In other embodiments, a private data server may receive a first set of programmatic model instructions to create a first model, and another private data server may receive a second set of programmatic model instructions to create a second model. Thus, the programmatic model instructions provided to each private data server 124 may be the same or different.

As proxy data 260 is generated and relayed to the global model server 130, the global model server aggregates the data and generates an updated global model. Once the global model is updated, it can be determined whether the updated global model is an improvement over the previous version of the global model. If the updated global model is an improvement (e.g., the predictive accuracy is improved), new parameters may be provided to the private data servers via the updated model instructions 230. At the private data server 124, the performance of the trained actual model (e.g., whether the model improves or worsens) can be evaluated to determine whether the models instructions provided by the updated global model result in an improved trained actual model. Parameters associated with various machine learning model versions may be stored so that earlier machine learning models may be later retrieved, if needed.

In still other embodiments, a private data server 124 may receive proxy related information (including for example proxy data 260, proxy data distributions 362, proxy model parameters 475, other proxy related data combined with seeds, etc.) from a peer private data server (a different private data server 124). The private data server may generate models based on its own local private data, or based on both its own local private data and the received proxy related information from a peer private data server. If the predictive accuracy of the combined data sets is improved, then the data sets or learned knowledge are combined.

In some embodiments, the information (e.g., machine learning models including trained proxy models, trained actual models, private data distributions, synthetic/proxy data distributions, actual model parameters, proxy model parameters, similarity scores or any other information generated as part of the machine learning process, etc.) can be geostamped (associated with a location or other identifier indicating where the processing occurred), timestamped, or integrated into a blockchain to archive research (see also US20150332283). Blockchains may be configured as sample-specific audit trails. In this example, the blockchain is instantiated as a single stand-alone chain for a single sample and represents the sample's life cycle or audit trail. Additionally, as the system can continuously receive new data in an asynchronous manner, geostamping can help manage inflow of new information (e.g., for a newly added clinic, all data geostamped as being from the clinic would be incorporated into the machine learning system. It is contemplated that any type of data may be geostamped.

Figure 2:
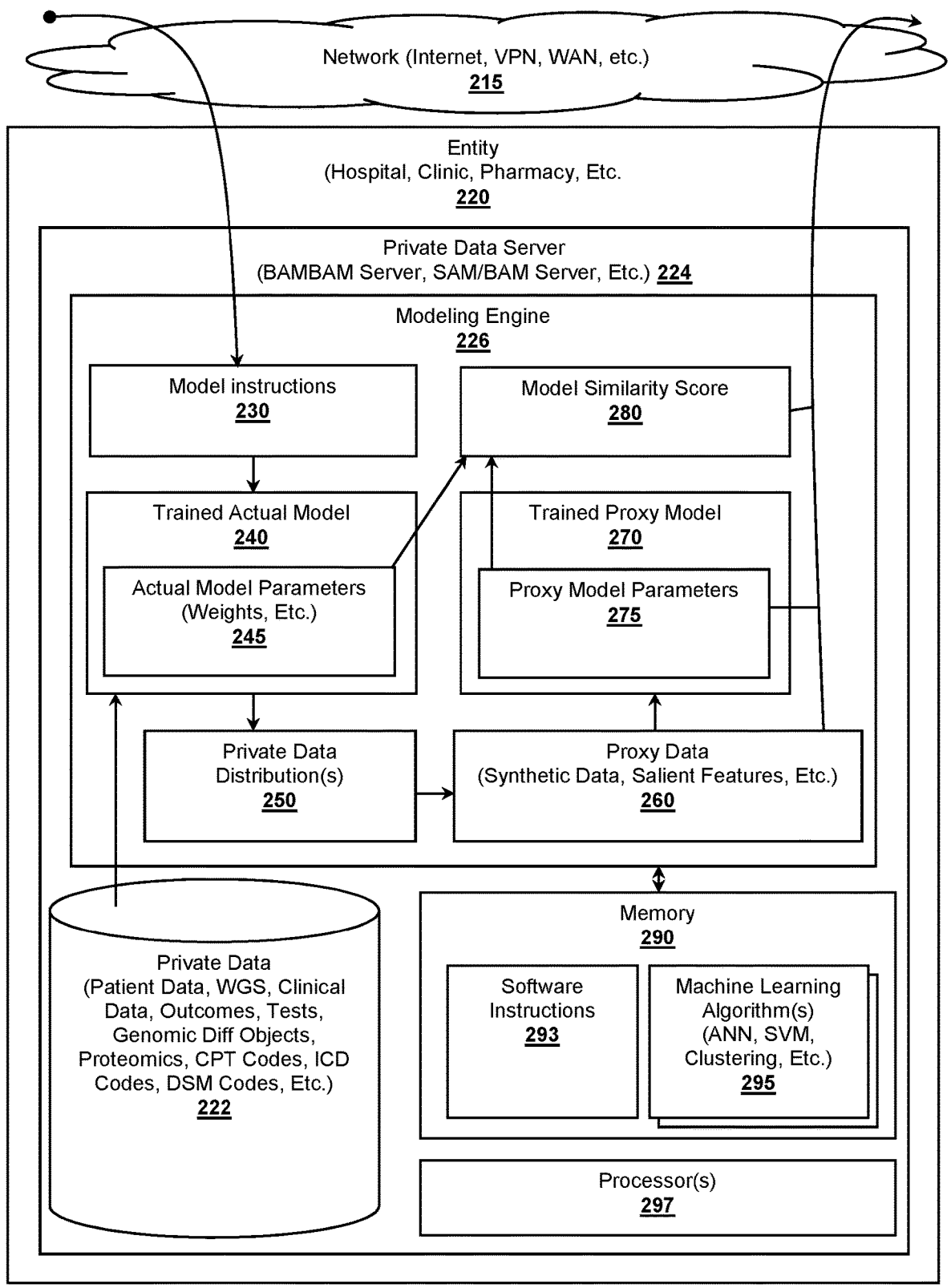
FIG. 2 is an example machine learning modeling engine architecture deployed within a private data server, according to the embodiments presented herein.

FIG. 2 is an illustration of an example architecture including private data server 224 within an entity 220 with respect to its machine learning activities. The example presented in FIG. 2 illustrates the inventive concepts from the perspective of how private data server 224 interacts with a remote computing device and private data 222. In more preferred embodiments, private data 222 comprises local private healthcare data, or more specifically includes patient-specific data (e.g., name, SSN, normal WGS, tumor WGS, genomic diff objects, a patient identifier, etc.). Entity 220 typically is an institution having private local raw data and subject to restrictions as discussed above. Example entities include hospitals, labs, clinics, pharmacies, insurance companies, oncologist offices, or other entities having locally stored data. Private data server 224 represents a local server, typically located behind a firewall of the entity 220. Private data server 224 can be embodied as a computer having one or more processors 297 that are configured to execute software instructions 293 stored in memory 290. Example servers that can be leveraged for the inventive subject matter include Linux® servers, Windows® servers, or other servers.

The private data server 224 provides access to private data 222 on behalf of the stakeholders of entity 220. In more preferred embodiments, private data server 224 represents a local cache of specific patient data, especially data sets of large sizes. For example, a patient might be undergoing various treatments for cancer or might be participating in a clinical trial. In such a scenario, the patient's data could include one or more genomic sequence data sets where each data set might include hundreds of gigabytes of data. If there are several patients, the total data set could represent many terabytes or more. Example genomic sequence data sets could include a whole genome sequence (WGS), RNA-seq data, whole exome sequence (WES), proteomic data, differences between tissues (e.g., diseased versus matched normal, tumor versus matched normal, one patient versus another, etc.) or other large data sets. Still further, a patient could have more than one genomic sequence data set on file; a tumor WGS as well as a matched normal WGS. One data sets that is particularly interesting includes genomic differences between a tumor sequence and that of a matched normal sometimes referred to as "genomic diff objects". Such genomic diff objects and their generation are described more fully in U.S. Pat. Nos. 9,652,587 and 9,646,134 to Sanborn et al., both titled "BAMBAM: Parallel comparative Analysis of High Throughput Sequencing Data" and filed May 25, 2011 and Nov. 18, 2011, respectively. Another type of data includes inferred proteomic pathways derived from patient samples as described in U.S. patent application publications 2012/0041683 and 2012/0158391 to Vaske et al. both titled "Pathway Recognition Algorithm Using Data Integration on Genomic Models (Paradigm)", filed on Apr. 29, 2011 and Oct. 26, 2011, respectively.

Providing a local cache of such large data sets via private data server 220 is considered advantageous for multiple reasons. The data sets are of such size that it is prohibitive to obtain such datasets easily on-demand or when immediately required. For example, a full WGS of a patient with a 50× read could comprise roughly 150 GB of data. Coupled with a similar WGS of a patient's tumor, the data set could easily be over 300 GB data. Naturally this assumes that there is only a single tumor WGS and a single normal WGS. If there are multiple samples taken at different tumor locations or at different times, the data set could easily exceed a Terabyte of data, just for one patient. The time to download such large datasets or access the datasets remotely far exceeds the urgency required when treating the patient in real-time. Thus, the patient and other stakeholders are best served by having local caches of the patient's data. Still, further is it impracticable to move the data in real-time as the patient moves or otherwise engages with various entities. As an alternative to providing cached data, for large data sets that may not fit within caches, mini Monte Carlo simulations that mimic private data can be used. These types of simulations typically utilize a seed, allowing synthetic private data to be generated with a Monte Carlo simulation in a deterministic fashion, based on parameters of the seed and pseudo random number generators. Once a seed is identified that generates the preferred amount of synthetic private data with minimal modification of the data, the seed can then be provided to any private data server 124, where it is used to regenerate the synthetic private data using the same pseudo random number generators and other algorithms. Synthetic data may be analyzed to ensure that it does not contain identifying features that should be kept private.

In the example shown, software instructions 293 give rise to the capabilities or functionality of modeling engine 226. Modeling engine 226 uses private data 222 to train one or more implementations of machine learning algorithms 295. Example sources of implementations of machine learning algorithms include sci-kit learn, Google®'s Artificial Intelligence including TensorFlow™, OpenAI™, Prediction IO™, Shogun™, WEKA, or Mahout™, Matlab, Amazon's Machine Learning, Microsoft's Azure Machine Learning, and SciKit-Learn, just to name a few. The various elements depicted within the modeling engine 226 represent the interaction of data and various functional modules within modeling engine 226. Thus, modeling engine 226 is considered a local agent configured to provide an interface to private data 222 as well as a conduit through which remote researchers over network 215 can create a locally trained model within modeling engine 226. In a very real sense, modeling engine 226 is a transformation module that converts local, private data 222 to knowledge about the data that can be consumed by external computing devices without comprising privacy. Knowledge can include any information produced by the machine learning system that has been de-identified.

Private data server 224 can take on many different forms. In some embodiments, private data server 224 is a computing appliance integrated within the IT infrastructure of entity 220, a dedicated server having its own storage system for private data 222 for example. Such an approach is considered advantageous in circumstances where private data 222 relates to large data sets that are targeting specific research projects external to entity 220. For example, the appliance could store patient data that is highly relevant to government or clinical studies. In other embodiments, private data server 224 can include one or more servers owned by and operated by the IT department of entity 220 where the servers include additional software modeling engine applications that can be deployed on the servers of entity 220.

In the example shown, private data server 224 is illustrated as a computing device configurable to communicate over network 215. For the sake of discussion, network 215 is considered the Internet. However, network 215 could also include other forms of networks including VPNs, Intranets, WAN, P2P networks, cellular networks, or other forms of network. Private data server 224 is configurable to use one or more protocols to establish connections with remote devices. Example protocols can be leveraged for such communications include HTTP, HTTPS, SSL, SSH, TCP/IP, UDP/IP, FTP, SCP, WSDL, SOAP, or other types of well-known protocols. It should be appreciated that, although such protocols can be leveraged, it is contemplated that the data exchanged among the devices in the ecosystem/system will be further packaged for easy transport and consumption by the computing devices. For example, the various data elements exchange in the system (e.g., model instructions 230, proxy data 260, etc.) can be packaged via one or more markup languages (e.g., XML, YAML, JSON, etc.) or other file formats (e.g., HDF5, etc.).

In some embodiments, private data server 224 will be deployed behind network security infrastructure; a firewall, for example. In such cases, a remote computing device will likely be unable to establish a connection with private data server 224 unless a suitable network address translation (NAT) port has been created in the firewall. However, a more preferable approach is to configure private data server 224, possibly via modeling engine 226, to reach out through the firewall and establish a communication link with a central modeling server (e.g., non-private computing device 130 of FIG. 1). This approach is advantageous because it does not require modification of the firewall. Still, the communication link can be secured through encryption (e.g., HTTPS, SSL, SSH, AES, etc.).

Modeling engine 226 represents an agent operating within private data server 224 and is configurable to create trained machine learning models. In some embodiments, modeling engine 226 can function within a secured virtual machine or secured container that is dedicated to specific research tasks, which allows multiple, disparate researchers to work in parallel while also ensuring that each researcher's efforts remain secure from each other. For example, modeling engine 226 can be implemented via a Docker® container, where each researcher would have a separate instance of their own modeling engine 226 running on private data server 224. In other embodiments, the modeling engine 226 can be constructed to process many sessions in parallel, where each session can be implemented as separate threads within the operating system (e.g., Linux, Windows, etc.) of private data server 224.

Once communication links are established among private data server 224 and one or more remote non-private computing devices, modeling engine 226 is ready to offer its services to outside entities; the researcher, for example. Modeling engine 226 receives one or more of model instructions 230 that instruct modeling engine 226 to create a trained actual model 240 as function of at least some of private data 222. For example, in some embodiments such as a neural net, inputs and other configuration parameters may be provided by model instructions, and the weights of each input determined by the machine learning system. Trained actual model 240 is a trained machine learning model trained from an implementation of machine learning algorithm 295. After training is complete, trained actual model 240 comprises one or more trained model parameters 245.

Modeling engine 226 receives model instructions to create a trained actual model 240 from at least some local private data 222 and according to an implementation of machine learning algorithm 295. Model instructions 230 represents many possible mechanisms by which modeling engine 226 can be configured to gain knowledge from private data 222 and can comprise a local command generated within entity 220, a remote command sourced over network 215, an executable file, a protocol command, a selected command from a menu of options, or other types of instructions. Model instructions 230 can vary widely depending on a desired implementation. In some cases, model instructions 230 can include streamed-lined instructions that inform modeling engine 226 on how to create the desired trained models, possibly in the form of a script (e.g., Python, Ruby, JavaScript, etc.). Further, model instructions can include data filters or data selection criteria that define requirements for desired results sets created from private data 222 as well as which machine learning algorithm 295 is to be used. Consider a scenario where a researcher wishes to research which patients are responders or non-responders to various drugs based on a support vector machine (SVM) in view of a specific genome difference between the patient's tumor sequence and the patient's matched normal sequence. Model instructions 230 for such a case can include, possibly packaged via XML or HDF5, the requirements for the data to be selected from private data 222, identified drug, reference to specific genomic diff object(s), indication of response vs. non-response, etc. Model instructions 230 can also include a specific reference to the desired SVM, possibly by an identifier (e.g., number, name, GUID, etc.) and version number, or even a pre-packed implementation of the SVM prepared for modeling engine 226 to execute.

In some embodiments, an application configured to collect metadata can scan private data to determine the types of data that are stored in the private data repository. For example, this application can scan file repositories to identify the type of files present (e.g., to identify filename extensions specific to a particular program indicating that a particular type of data is available, scan file names that are named according to a naming convention to indicate the type of data that is available, etc.). In other embodiments, the application may interface with a database to query the types of available data, or alternatively, the database may be configured to send a report reflecting the types of data available, to the global modeling server 130. Once a description of the metadata (reflecting the private data) is available, model instructions can then be configured to make reference to the private data, thereby providing instructions regarding selection of inputs to the machine learning systems. In cases in which a query by a researcher is ongoing and continuously updated, e.g., at periodic intervals, the system can be configured to recognize the metadata, determine whether key parameters are present, and then cause generation and transmission of model instructions corresponding to the query set up by the researcher. In other cases, for novel queries, a researcher may generate the model instructions in a manual or semi-automated manner. For new queries, the system may be configured to provide recommendations regarding types of data to analyze in order to generate model instructions for such new queries.

Metadata from each private data server can be provided to the global model server. The metadata returns the attribute space (and not raw or private data). Based on this information, the researcher generating the machine learning task(s) can configure model instructions for a particular private data server to analyze a particular set of private data.

In some embodiments, the private data server may recognize that model accuracy is low, and may request additional updates from the global model server. The global model server using the global modeling engine aggregates data from different locations into a global model. For example, if an improved cancer survival model is requested, and data of the same type is not available, data from different tissue types may be combined to improve predictive accuracy of the cancer survival model.

It is also possible for model instructions 230 to take on a much more complex nature. More specifically, model instructions 230 could be self-contained wherein it actually includes a complete modeling package including a query engine (e.g., SQL, NoSQL, etc.) specifically configured to interface with the local database, a pre-compiled (e.g., object code, byte codes, etc.) implementation of machine learning algorithm 295, rules for managing resulting models, and so on. Such an approach can be implemented via a packaged and deliverable container. It should be further appreciated and it is fully considered that model instructions 230 can also vary within the spectrum from a simple configuration to a more complex configuration presented. Thus, model instructions 230 can include a local command received from a local computer, a remote command received from a computer (e.g., a peer data server or a global model server) over network 215, an executable file, a protocol command, a selected command from a menu of options, a remote procedure call, or other types of instructions.

Modeling engine 226 leverages the data selection criteria from model instructions 230 to create a result set from private data 222, possibly via submitting a query to the database storing private data 222. For example, the query could include a SQL query properly formatted from the requirements in model instructions 230 to access or retrieve the attributes or tables stored in private data 222. The results set could be the same exact data as private data 222 or a proper subset depending on the nature of the data selection criteria. The results set becomes the training data for trained actual model 240. That is, the results set may be used to train actual model 240. Within the context of health care, the results set includes patient data that could also include one or more of the following patient specific information: symptoms, tests, test results, provider names, patient name, age, address, diagnosis, CPT codes, ICD codes, DSM codes, relationships, or other information that can be leveraged to describe the patients. It should be appreciated that the results set does not require a pre-processing de-identification step to sanitize the data, as the machine learning algorithm operates on local private data. The disclosed approach is considered superior to previous approaches because retaining the patient-specific information allows modeling engine 226 to gain knowledge from trained actual models 240 that might be lost otherwise. For example, if patient names are removed prior to analysis by the modeling engine 226, then relevant family history may not be able to be incorporated into the actual model 240 as a predictive parameter.

Modeling engine 226 creates trained actual model 240 as a function of the results set representing at least some of private data 222. This is achieved by modeling engine 226 training the desired implementation of machine learning algorithm 295 on the private data 222 results set. In view that the desired machine learning algorithm 295 could include a wide variety of possible algorithms, model instructions 230 can include instructions that define the condition under which training occurs. For example, the conditions could include a number of iterations or epochs to execute on the training data, learning rates, convergence requirements, time limits for training, initial conditions, sensitivity, specificity or other types of conditions that are required or optional. Convergence requirements can include first order derivatives such as "rates of change", second order derivatives such as "acceleration", or higher order time derivatives or even higher order derivatives of other dimensions in the attribute space of the data, etc.

Machine learning algorithms 295 can include quite a large number of different types of algorithms including implementations of a classification algorithm, a neural network algorithm, a regression algorithm, a decision tree algorithm, a clustering algorithm, a genetic algorithm, a supervised learning algorithm, a semi-supervised learning algorithm, an unsupervised learning algorithm, a deep learning algorithm, or other types of algorithms. More specifically, machine learning algorithms 295 can include implementations of one or more of the following algorithms: a support vector machine, a decision tree, a nearest neighbor algorithm, a random forest, a ridge regression, a Lasso algorithm, a k-means clustering algorithm, a boosting algorithm, a spectral clustering algorithm, a mean shift clustering algorithm, a non-negative matrix factorization algorithm, an elastic net algorithm, a Bayesian classifier algorithm, a RANSAC algorithm, an orthogonal matching pursuit algorithm, bootstrap aggregating, temporal difference learning, backpropagation, online machine learning, Q-learning, stochastic gradient descent, least squares regression, logistic regression, ordinary least squares regression (OLSR), linear regression, stepwise regression, multivariate adaptive regression splines (MARS), locally estimated scatterplot smoothing (LOESS) ensemble methods, clustering algorithms, centroid based algorithms, principal component analysis (PCA), singular value decomposition, independent component analysis, k nearest neighbors (kNN), learning vector quantization (LVQ), self-organizing map (SOM), locally weighted learning (LWL), apriori algorithms, eclat algorithms, regularization algorithms, ridge regression, least absolute shrinkage and selection operator (LASSO), elastic net, classification and regression tree (CART), iterative dichotomiser 3 (ID3), C4.5 and C5.0, chi-squared automatic interaction detection (CHAID), decision stump, M5, conditional decision trees, least-angle regression (LARS), naive bayes, gaussian naive bayes, multinomial naive bayes, averaged one-dependence estimators (AODE), bayesian belief network (BBN), bayesian network (BN), k-medians, expectation maximisation (EM), hierarchical clustering, perceptron back-propagation, hopfield network, radial basis function network (RBFN), deep boltzmann machine (DBM), deep belief networks (DBN), convolutional neural network (CNN), stacked autoencoders, principal component regression (PCR), partial least squares regression (PLSR), sammon mapping, multi-dimensional scaling (MDS), projection pursuit, linear discriminant analysis (LDA), mixture discriminant analysis (MDA), quadratic discriminant analysis (QDA), flexible discriminant analysis (FDA), bootstrapped aggregation (bagging), adaboost, stacked generalization (blending), gradient boosting machines (GBM), gradient boosted regression trees (GBRT), random forest, or even algorithms yet to be invented. Training may be supervised, semi-supervised, or unsupervised. In some embodiments the machine learning systems may use Natural Language Processing (NPL) to analyze data (e.g., audio data, text data, etc.). Once trained, trained actual model 240 represents what has been learned or rather the knowledge gained from private data 222 as desired by the researcher submitting the machine learning job. Trained actual model 240 can be considered a passive model or an active model. A passive model represents the final, completed model on which no further work is performed. An active model represents a model that is dynamic and can be updated based on various circumstances. In some embodiments, the trained actual model 240 is updated in real-time, on a daily, weekly, bimonthly, monthly, quarterly, or annual basis. As new information is made available (e.g., to update model instructions 230, shifts in time, new or corrected private data 222, etc.), an active model will be further updated. In such cases, the active model carries metadata that describes the state of the model with respect to its updates. The metadata can include attributes describing one or more of the following: a version number, date updated, amount of new data used for the update, shifts in model parameters, convergence requirements, or other information. Such information provides for managing large collections of models over time, where each active model can be treated as a distinct manageable object.

Trained actual model 240 is referenced using the term "actual" to clarify that it is trained on real data that has not been de-identified and that is considered to be the actual data obtained from private data 222. This is in contrast to trained proxy model 270, discussed further below, that is trained on proxy data 260, which can be considered simulated data.

Trained actual model 240 comprises multiple points of interest. First, although not shown, trained actual model 240 can include metadata as discussed previously that describes the nature of the trained model. Second, trained actual model 240 comprises a number of parameters as represented by actual model parameters 245. Actual model parameters 245 are the specific values that are used by trained actual model 240 for prediction purposes when operating on live data. Thus, actual model parameters 245 can be considered an abstract representation of the knowledge gained from creating trained actual model 240 from private data 222. When actual model parameters 245 are packaged and transmitted to remote non-private computing devices or to peer private data servers, the remote non-private or peer computing devices can accurately reconstruct trained actual model 240 via instantiating a new instance of trained actual model 240 from the parameters locally at the remote computing device without requiring access to private data 222, thus eliminating the need for de-identification. Actual model parameters 245 depend on the nature of the trained actual model 240 and its underlying implementation of machine learning algorithm 295 as well as the quality of the private data 222 used to generate actual model 240. Examples of actual model parameters 245 include weights, kernels, layers, number of nodes, sensitivities, accuracies, accuracy gains, hyper-parameters, or other information that can be leveraged to re-instantiate trained actual model 240.

In some embodiments where the amount of private data 222 is considered of high quality and is of sufficient size, transmitting actual model parameters 245 to a remote device can be of great benefit. However, one should further appreciate that entity 220 might not have a sufficiently large amount of local data to complete a research task. Further, another issue that is addressed according to the techniques disclosed herein includes how to integrate the knowledge gained from the trained actual model 240 with data from other entities 220, and in particular on how to aggregate knowledge among peers in the ecosystem to generate knowledge pertaining to model instructions reflecting the interests of the researcher or clinician. In the example shown, these points are addressed through configuration modeling engine 226 to gain an understanding of the data used to create trained actual model 240.

In the example shown, modeling engine 226 analyzes the training data set used to create trained actual model 240 in order to generate an understanding of the nature of the training data set as represented by private data distributions 250. Thus, modeling engine 226 is further configurable to generate a plurality of private data distributions 250 that represent the local private data in aggregate used as a training set to create trained actual model 240. In some embodiments, modeling engine 226 can automatically execute many different algorithms (e.g., regressions, clustering, etc.) on the training data sets in an attempt to discover, possibly in an unsupervised manner, relationships within the data that can be represented via private data distributions 250. Private data distributions 250 describe the overall nature of the private data training set. For example, private data distributes 250 could include a histogram of patients' ages. A more detailed discussion regarding private data distributions 250 is presented with respect to FIG. 3 as discussed below. Private data distributions 250 can be continuous, discontinuous, discreet, or other types of distributions. Private data distributions can include distributions, including but not limited to, Bernoulli distributions, Rademacher distributions, binomial distributions, beta-binomial distributions, degenerate distributions, discrete uniform distributions, hypergeometric distributions, and Poisson binomial distributions. Private data distributions can also include beta negative binomial distributions, Boltzmann distributions, Gibbs distributions, Maxwell-Boltzmann distributions, Borel distributions, Champernowne distributions, extended negative binomial distributions, extended hypergeometric distributions, log-series distributions, logarithmic distributions, negative binomial distributions, compound Poisson distributions, parabolic fractal distributions, Poisson distributions, Polya-Eggenberger distributions, skew elliptical distributions, Yule-Simon distributions, and zeta distributions. Private data distributions can also include arcsine distributions, beta distributions, logitnormal distributions, uniform distributions, Irwin-Hall distributions, Bates distributions, Kent distributions, logarithmic distributions, Marchenko-Pastur distributions, density distributions, raised cosine distributions, reciprocal distributions, triangular distributions, trapezoidal distributions, truncated normal distributions, U-quadratic distributions, and von Mises-Fisher distributions. Still other forms of distributions include continuous uniform distributions, Skellam distributions, Chi-squared distributions, gamma distributions, or any other form of distributions used in the statistical sciences.

Modeling engine 226 generates a set of proxy data 260 according to private data distributions 250 to create a simulated or Monte Carlo data set that can be leveraged in an attempt to re-create the knowledge gained via training trained actual model 240. Generating proxy data 260 aids in reducing or eliminating the need for de-identification of private data 222 training set. Proxy data 260 can be considered synthetic data randomly generated, in some cases deterministically generated, that retains the learnable salient features (i.e., knowledge) of the training data while eliminating the references to real information stored in private data 222. Some embodiments compare samples from proxy data 260 to samples within private data 222 to ensure that the proxy samples lack sufficient overlap with actual patient data. Proxy samples having significant overlap can be discarded to ensure privacy is maintained. The proxy sample exclusion filter can be based on criteria defined according to the namespace or attribute space of the patient data within private data 222. For example, a proxy sample could be eliminated if has too many features in common with one or more actual samples (e.g., common zip codes, common symptoms, etc.).

In some embodiments, during generation of a proxy data set, a known "seed" can be implemented so that generation of the proxy data set is deterministic. Thus, the model parameters and the seed can be sent to a peer device or a non-private device allowing an exact duplicate of the proxy data to be generated at another location. A source for truly random seeds can be found at URL www.random.org.

In some aspects, the trained machine learning model and proxy data generation can be considered as a form of lossy compression. Similar to lossy compression, transformation of original data into proxy data preserves key characteristics of the data, but does not retain granularity with regard to individual patients. By delivering a set of model parameters, a form of customized compression, the data can be recreated based upon the parameters. Rather than sending all of the proxy data sets to a peer server, the model parameters (machine learned parameters based on a data distribution, which is effectively a compressed version of the data set) can be sent along with a seed. The local machine receives the model parameters and seed and re-creates the deterministic proxy data.

Thus, generation of proxy data provides a clear improvement to the field of data science, artificial intelligence, and distributed computing. As proxy data is a synthetic equivalent of actual data, this data may be provided in a more compact form as compared to a large set of data, thus, improving the performance of the artificial intelligence platform used to aggregate data sets throughout a distributed computing environment. For example, providing a parameter in the form of a distribution, versus millions of actual individual data points, results in a compact data representation on which an artificial intelligence platform can operate much more efficiently, thereby improving the overall functioning of the system. Of course, as discussed herein, proxy data preserves knowledge that might otherwise be discarded during the de-identification process. Further, patient privacy and compliance with HIPPA standards may be maintained by using proxy data.

Modeling engine 226 then creates trained proxy model 270 from proxy data 260 by training the same implementation of machine learning algorithm 295 used to create trained actual model 240 except on proxy data 260. Trained proxy model 270 also comprises proxy model parameters 275, which likely differ slightly from actual model parameters 245. In some embodiments, modeling engine 226 iteratively generates proxy data 260 and creates trained proxy model 270 until trained proxy model 270 is sufficiently similar to trained actual model 240 based, at least in part on the trained model's parameters. This approach is considered advantageous because it provides for generating synthetic data capable of reproducing the knowledge gained from private data 222 as represented by the two trained models.

The similarity between trained proxy model 270 and trained actual model 240 can be measured through various techniques by modeling engine 226 calculating model similarity score 280 as a function of proxy model parameters 275 and actual model parameters 245. The resulting model similarity score 280 is a representation of how similar the two models are, at least to within similarity criteria. The similarity criteria can be defined by the researcher requesting the analysis of private data 222 and can be delivered within model instructions 230. In some embodiments, similarity score 280 can be a single value (e.g., a difference in accuracy, sum of squared errors, etc.) that can then be compared to a threshold value. In other embodiments, similarity score 280 can be multivalued. For example, if many proxy models are generated, the similarity score might include an average value of accuracies of the proxy models relative to the actual models along with a width, assuming that the accuracies fall within a normal-like distribution. In embodiments where similarity score 280 does include multiple values, then the values within similarity score 280 can be compared to similarity criteria (i.e., multiple criterion). Techniques for measuring similarity score 280 are discussed further with respect to FIG. 4.

If similarity score 280 satisfies the similarity criteria thereby indicating that the trained proxy model 270 is sufficiently similar to the trained actual model 240, modeling engine 226 can then transmit information about the knowledge gained from the effort. More specifically, for example, once the similarity criteria has been satisfied, modeling engine 226 can transmit, e.g., according to model instructions 230, one or more of proxy data 260, proxy model parameters 275, similarity score 280, or other information to a non-private computing device located over network 215. This approach, as discussed previously, allows for a researcher to gain knowledge about private data 222 without compromising its privacy or security.

The non-private computing device that receives the knowledge can then aggregate the knowledge with knowledge gained from other private data servers 224. One should appreciate that the non-private computing device (see FIG. 1, non-private computing device 130) could also be a different private data server in the ecosystem, a centralized machine learning hub or service, a global modeling engine, a cloud-based service, or other type of computing device suitably configured to receive the data. From the perspective of a central modeling service operating as the non-private computing device, the central modeling service can aggregate all the proxy data sets as a new aggregated training data set to create a trained global aggregated model. The aggregated model can then be transmitted back to interested stakeholders, private data server 224 for example, for use as a classifier or predictor of patient treatments and outcomes. Additionally, the aggregated model can be used as a baseline or foundation for new versions of trained actual model 240. Said from a different perspective, modeling instructions 230 could include a global trained model, which can then be further trained on private data 222 to generate trained actual model 240. The global trained model could also be the foundation for trained proxy model 270 as well.

Figure 3:
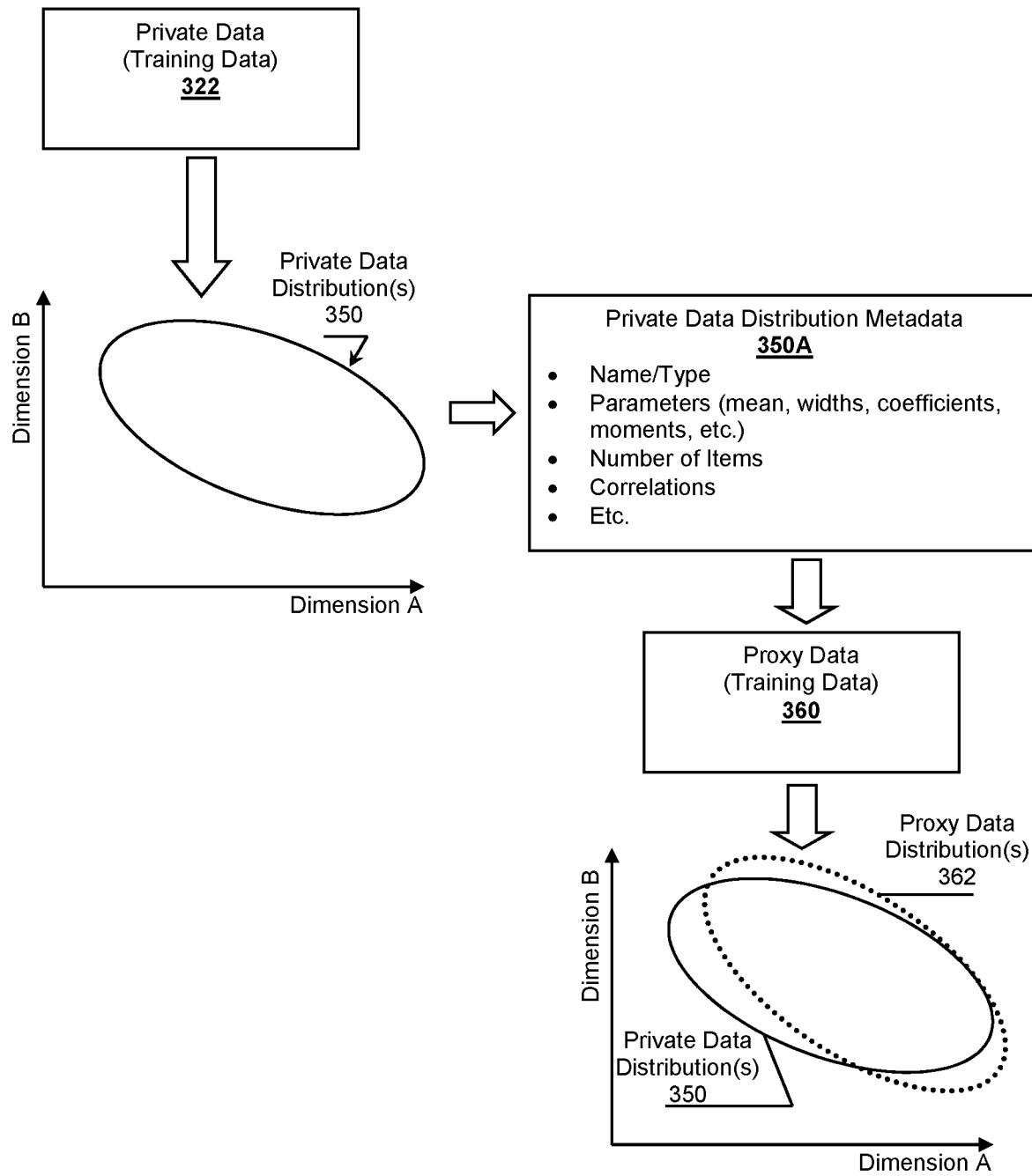
FIG. 3 is a flowchart showing generation of proxy training data in preparation for building a proxy trained model, according to the embodiments presented herein.

FIG. 3 presents additional details regarding the nature of private data distributions and the creation of proxy data. Private data 322 represents a training data set used to create a trained actual model and is considered to be the input data set after any optional or required preprocessing has been completed; correcting for factual errors in private data 322 for example. Private data 322 can comprise many dimensions or attributes where each sample in private data 322 could include many values according to the attribute space of the data. With respect to health care, private data 322 could include one or more of the following types of data, including but not limited to: genomic data, whole genome sequence data, whole exosome sequence data, proteomic data, neoepitope data, RNA data, allergy information, encounter data, treatment data, outcome data, appointment data, order data, billing code data, diagnosis code data, results data, demographic data, medication data, vital sign data, payor data, drug study data, drug response data, longitudinal study data, biometric data, financial data, proprietary data, electronic medical record data, research data, human capital data, performance data, analysis results data, event data, or other types of data. Thus, a single sample within private data 322 could represent a single patient and the patient's specific set of attributes or information, either public or private.

In aggregate, all the samples in private data 322 form one or more of private data distributions 350 according to each relevant dimension in the training data set. For example, private data distributions 350 could include a distribution of ages, weights, types of mutations in tumor sequences, tumor versus matched normal genomic differences, or other information. Although the term "distribution" is used with respect to private data distributions 350, it should be appreciated that there can be many different types of distributions. For example, distribution of gender would likely be two numbers: the number of females and the number of males in private data 322. Still, private data distributions 350 can also include well defined types of mathematical or statistical distributions, possibly including a Gaussian distribution, a Poisson distribute, a Bernoulli distribution, a Rademacher distribution, a discrete distribution, a binomial distribution, a zeta distribution, a Gamma distribution, a beta distribution, a histogram distribution, or other types of distributions. In other embodiments, private data distributions 350 can also comprise one or more covariant matrices among dimensions of relevance.

In other embodiments, data distributions may be manually constructed (e.g., a histogram, a probability density function, etc.). In some other embodiments, data distributions may be based on rates of change, and/or higher order derivatives (e.g., moments).

For clarity and the sake of discussion, private data distributions 350 are represented in FIG. 3 in a graph as having two dimensions; A and B. The graph indicates that there is a weak correlation between the two dimensions. This indication is presented to demonstrate that private data distributions 350 can include one more correlations among the various attributes or dimensions in the private data 322, which preferably is preserved when creating proxy data 360. Such correlations can be discovered through various techniques including regression, principle component analysis, Pearson's correlations, k-means clustering, or other techniques that can be leveraged for identifying relationships among dimensions in the training data.

It should also be appreciated that private data distributions 350 can include additional information as shown by private data distribution metadata 350A. Metadata 350A is information about the nature of the discovered private data distributions 350 and that can be encapsulated and transmitted to other computing devices. Example metadata includes a name or type of distribution, parameters defining the distribution (e.g., mean, mode, median, width, silhouette coefficients, $\chi^2$ fits, Pearson coefficients, moments, etc.), number of samples in the distribution, correlations (e.g., principle components, etc.), or other information that can be used to define private data distributions 350.

Private data distributions 350 can be considered a type of probability distribution that can be leveraged to generate proxy data 360. For continuous distributions that can be fit to private data 322, the modeling engine can use metadata 350A for the continuous distribution (e.g., mean, width, moments, etc.) to randomly generate values for new samples for the dimension modeled by the continuous distribution within proxy data 360. For non-continuous distributions, a histogram for example, can be treated as a discreet probability density function to generate values for the relevant dimension. For example, consider zip codes. Patient data 322 could include a number of patient sample points across these multiple zip codes. A histogram can be generated for the relevant zip codes and the histogram can be normalized to form a zip code probability distribution. As a more specific example, considering a plurality of zip codes in which a subset of zip codes are associated with having a particular type of cancer, a histogram can be constructed of zip codes having a correlation with cancer. Synthetic patient data can be constructed reflective of the zip code probability distribution. The modeling engine uses the normalized zip code distribution to generate zip code values for proxy data 360.

If there are no discovered or apparent correlations, principle component analysis (PCA) can be leveraged to reduce the dimensionality of the private data 322. Once the dimensionality is reduced, a new trained actual model can be generated and compared to the original trained actual model to ensure that no knowledge has been lost after dimensional reduction and that accuracy in the model is maintained. Reducing the dimensionality of the data further improves performance of the computing system by decreasing compute time and by decreasing the transmission time. The comparison can be conducted using the similarity score techniques discussed in FIG. 4. The modeling engine can apply PCA to the data to reduce the dimensionality, and the modeling engine can also derive one or more eigenvectors or eigenvalues for private data 322. The "eigenvectors" can be used to represent the training data set. Thus, proxy data 360 can be considered as comprising combinations of the eigenvectors as derived from private data 322, private data distributions 350, actual model parameters, or other information related to private data 322. For example, a single sample within proxy data could include linear, possibly weighted, combination of the eigenvectors. Such combinations can be considered to include an eigenpatient, an eigenprofile, an eigendrug, an eigenhealth record, an eigengenome, an eigenproteome, an eigenRNA profile, an eigenpathway, or other type of vector depending on the nature of the data within private data 322.

In some embodiments, each eigenvector has a corresponding eigenvalue, such that the eigenvalue/eigenvector occur in pairs. The eigenvalue is a measure of the variance in a data set, and the eigenvector indicates a direction of the data in an n-dimensional space. For a given data set, the number of eigenvalue/eigenvectors pairs equal the dimensionality of the data set. Any and all such information can be utilized according to the techniques disclosed herein.

There are multiple points of interest associated with proxy data 360. Proxy data 360 is not necessarily required to have the same number samples as in private data 322. Rather, proxy data 360 need only have a sufficient number of samples so that proxy data 360 can sufficiently reproduce a model similar to the trained actual model. Another point of interest, as presented in FIG. 3, is that proxy data 360 can have different proxy data distributions 362, at least within acceptable or defined limits. The difference in the distributions could be slightly different due to the randomness in the newly generated samples relative to private data distribution 350 according to which the samples were created. Acceptable differences between proxy data distributions 362 and private data distributions 350 can be considered a hyperparameter that can be tuned to ensure proxy data 360 is capable of generating a desired similar model. Still, the differences between the distributions can be permitted to be more then negligible, as long as proxy data 360 generates a sufficiently similar trained proxy model to that of the trained actual model. Still another point of interest is that proxy data 360 can be generated iteratively until it has the desired characteristics; acceptable proxy data distribution 362 characteristics, acceptable similar models, or other factors. For example, the modeling engine can use a genetic algorithm to alter the values of proxy data 360 until a suitable similar trained proxy model emerges using the similarity score as a fitness function, or using differences between the actual data's covariance matrix and proxy data's 360 covariance matrix to ensure proxy data 360 retains the same or similar shape as the actual data. It is also considered acceptable to adjust or "mutate" the proxy data distributions 362 to achieve a better trained proxy model fit to the trained actual model.

As described herein, proxy data is based on private data distributions, and it is important to ensure that the proxy data mirrors the private data distributions. For example, for 5 dimensions (where each dimension may represent a different type of data distribution), the proxy data may be represented as a 5-tuple. The proxy data, which is synthesized, may be mapped to "fake" patients with fake records, having characteristics similar to real patients, and may be compared to patient data to ensure that it is a suitable representation of patient data.

Figure 4:
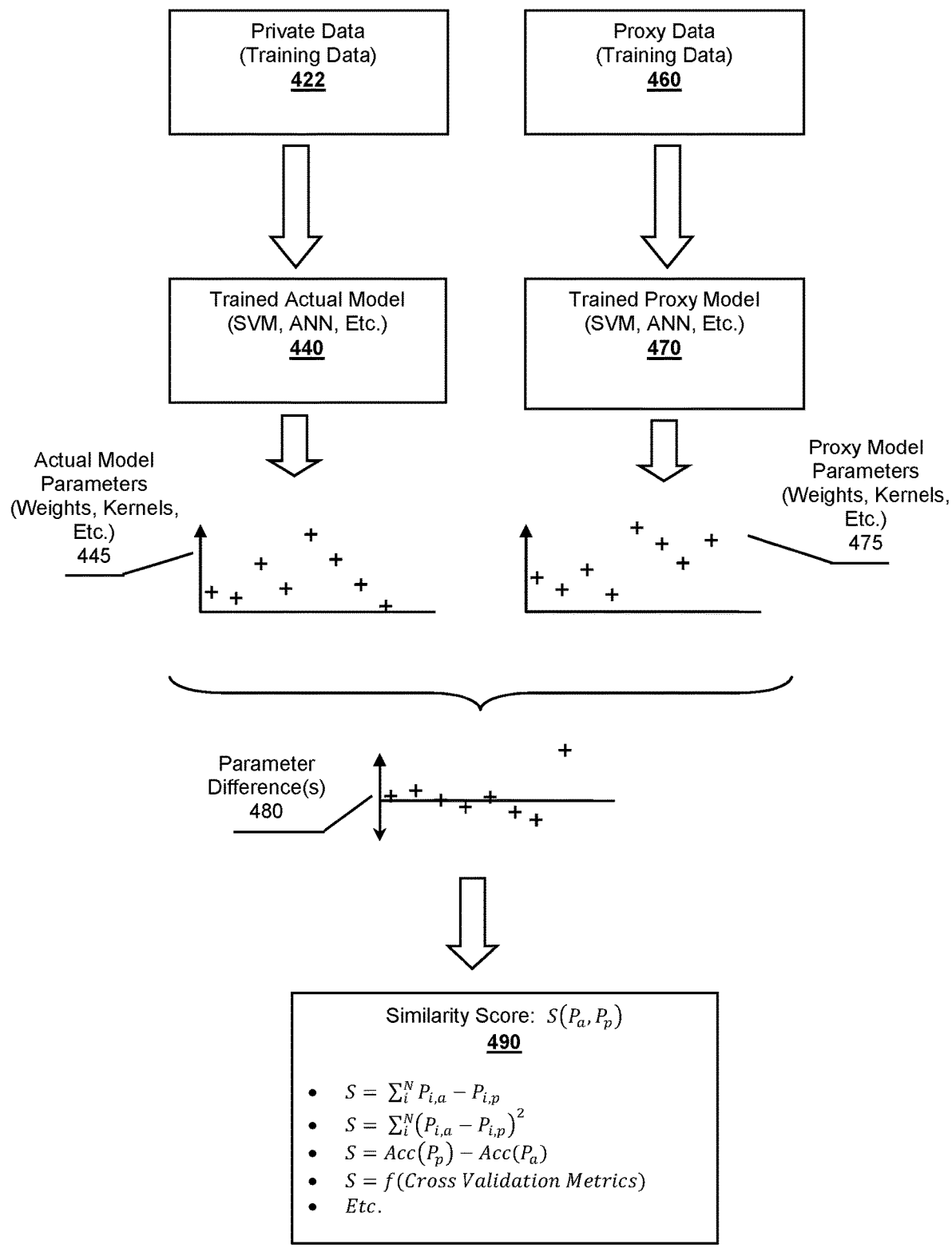
FIG. 4 is a flowchart showing generation of one or more similarity scores comparing the similarity of a trained actual model with a trained proxy model, according to the embodiments presented herein.

FIG. 4 illustrates possible techniques for calculating similarity score 490 between two trained models; trained actual model 440 and trained proxy model 470 in this example. Trained actual model 440 has been trained on real-world, actual private data 422 as discussed previously. Trained proxy model 470 has been trained on synthetic proxy data 460 constructed as a function of the data distributions of private data 422 as discussed with respect to FIG. 3.

Each of the trained models are considered to comprise corresponding model parameters that define necessary features (e.g., parameter values, number of parameters, number of layers, number of nodes, etc.) to create or re-instantiate the trained models. The model parameters depend on the nature of the underling implementation of the corresponding machine learning algorithm. For example, when trained actual model 440 comprises a 2D SVM, actual model parameters would likely include values for soft margin parameter C, kernel selection and its values, threshold value c, intercept, weights, or other SVM parameters. In the case of a neural network, actual model parameters could include the number of layers, kernel values, number of neurons/nodes in each layer, learning rates, momentum, epochs, weights of inputs, or other values that allow for re-instantiating the neural network.

Model parameters may also be included which prevent overfitting. For instance, the system may provide automated feedback as part of the defined modeling instructions to prevent over-trained or over-fitted local models. With advances in computing technology, e.g., neural nets that include a large number of neurons and multiple layers, machine learning systems can generate complex models that do not provide an optimal fit. For example, instead of a linear or lower order fit, a higher order fit (e.g., a $12^{th}$ degree polynomial) may be generated by a machine learning system that does not optimally categorize or characterize private data. To prevent overfitting, the number of nodes, number of layer, types of algorithms, etc. may be constrained by the model instructions used to generate the machine learning model. Other causes of overfitting include an insufficient amount of data from which to build a model. Thus, model parameters could include a small number of parameter values (e.g., 10 or less) or could include a very large number of parameter values (e.g., more than one million). Here, it is understood that in the case of 1 million parameters, this is still much smaller than transmitting the data set used to derive the 1 million parameters. It should be appreciated that proxy model parameters 475 should comprise the exact same number of parameters as actual model parameters 445 considering that the trained actual model and the trained proxy model 470 are built on the same underlying implementation of the same machine learning algorithm. However, the values for the various parameters can be different as represented by the two qualitative graphs. Considering that actual model parameters 445 and proxy model parameters 475 have the exact same number of parameters, they can be compared to each other on a one-to-one basis. In the example shown, the comparison is represented by difference parameters 480 where the parameter-wise difference is presented. If the trained proxy model 470 were completely identical to trained actual model 440, difference parameters 480 would all be zero. However, considering that the trained proxy model 470 is built on proxy data 460, non-zero differences are expected. Therefore, the two trained models can be compared, at least in the example shown, by calculating similarity score 490 as a function of the values of actual model parameters ($P_a$) 445 and proxy model parameters ($P_p$) 475, wherein in similarity score 490, N corresponds to the number of parameters and i corresponds to the $i^{th}$ parameter.

Similarity score 490 can be calculated through various techniques and according to the goals of a researcher as outlined in the corresponding model instructions. In some embodiments, similarity score 490 can be calculated based on the differences among the model parameters (e.g., parameters differences 480). For example, similarity score 490 could include the sum of the differences or the sum of the squares of the differences, a metric distance between parameters, a difference of covariance, differences of elements in covariance matrices, etc. The sum of the squares is considered more preferable in some circumstances over the sum of the differences. In cases where the parameters can have widely different definitions, the values can be normalized or weighted so that each difference contributes equally or according to their importance. Beyond parameter differences 480, similarity score 490 could also be based on other aspects of the trained models. Other non-difference values could include comparison of model accuracies based on one or more validation sets, model accuracy gains, data distributions, or other criteria.

Although similarity score 490 is illustrated as a single value, it should be appreciated that similarity score 490 could also be multi-valued, including two or more of any of the aforementioned difference or non-difference values. For example, the score could include both the sum of the differences as well as the average, possibly normalized, difference among the parameters.

Similarity score 490 can be tracked through multiple iterations of creating proxy data 460 and training proxy model 470 to ensure that similarity score 490 trends toward a desired direction. In this sense, similarity score 490 can represent a fitness value as the proxy data is generated. When similarity score 490 satisfies similarity transmission requirements, the modeling engine can then send proxy data 460, along with other ancillary information (e.g., proxy model parameters 475, actual model parameters 445, parameter differences 480, similarity score(s) 490, etc.), to a remote non-private computing device. In some embodiments, the non-private computing device operates as a global modeling engine configurable to aggregate proxy data 460 from many distributed peers into a global model. Through the disclosed approach, the knowledge gained from each set of private data 422 is retained while also ensuring that the private data 422 remains secured.

Figure 5:
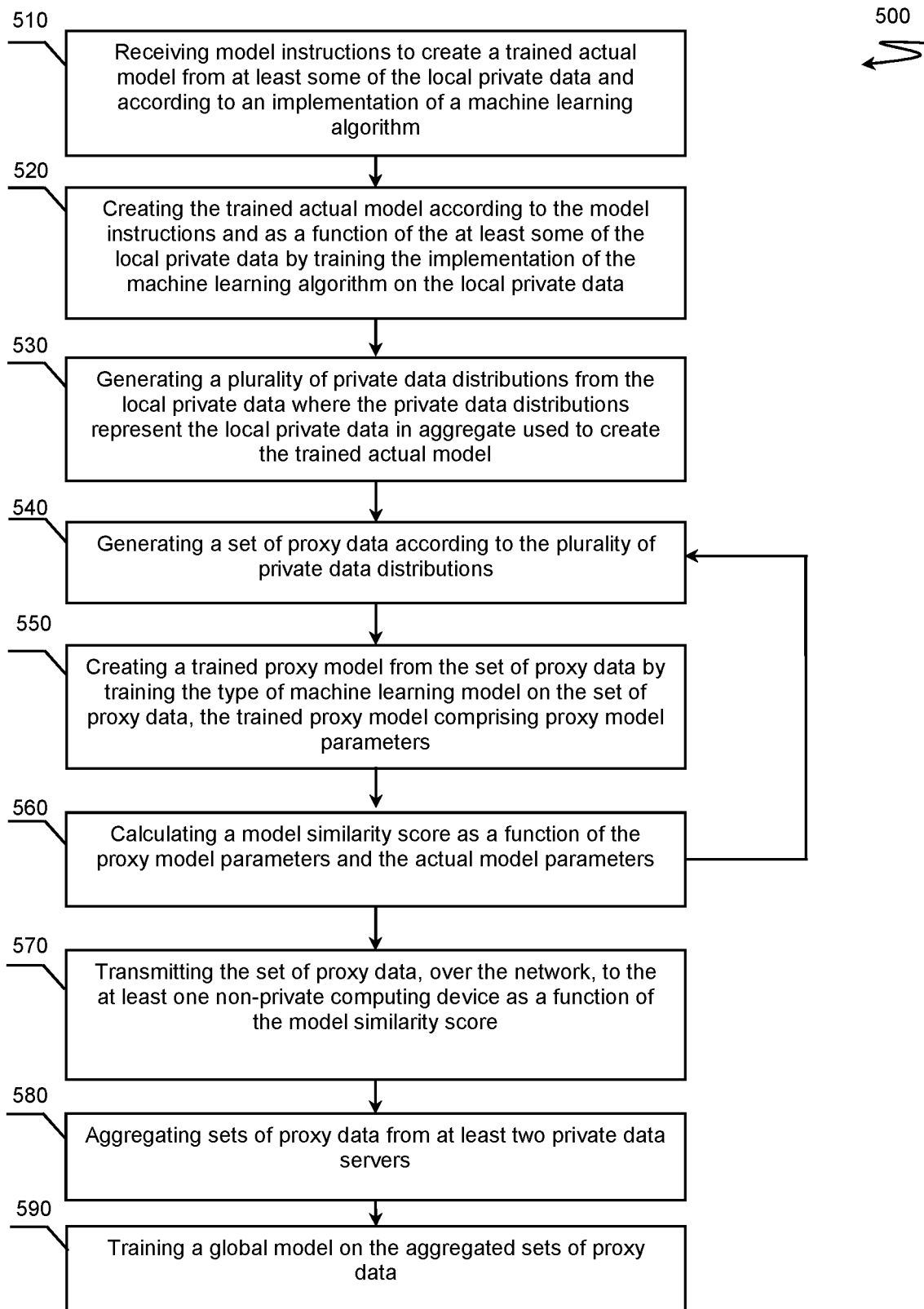
FIG. 5 is an operational flowchart showing an example method of distributed, online machine learning where private data servers generate proxy data capable of replicating the nature of a trained actual model generated on real data where the proxy data is transmitted to a non-private computing device, according to the embodiments presented herein.

Yet another technique for establishing similarity score 490 can include performing a cross validation on trained proxy model 470 using various relevant data sets. In some embodiments, the cross validation can be performed using different portions of private data 422 used as a training set for trained actual model 440. When the two trained models are sufficiently similar, the trained proxy model 470 will generate acceptable prediction results using the actual data. In other embodiments, proxy data 422 can be partitioned into training and validation data sets, which can then be used for cross-fold validation. Here, the training data 422 would be used to generate the trained actual model 440, and the private data distributions would be used to generate proxy data 460. The training proxy data would be used to generate the trained proxy model 470, and then the validation proxy data would be provided to the trained proxy model for validation. Still further, trained proxy model 470, possibly along with proxy model parameters 475, can be sent to other modeling engines in the ecosystem (e.g., in FIG. 1, other modeling engines 126, non-private computing device 130, global model engine 136, etc.). These computing devices can then attempt to validate trained proxy model 470 on their respective, possibly private, similar training data sets. Once each of the validating devices completes their validation efforts, results are provided back to the original modeling engine for evaluation and derivation of model similarity score 490. FIG. 5 presents a computer-implemented method 500 of distributed, online machine learning. Method 500 relates to building an aggregated trained global model from many private data sets. The trained global model can then be sent back to each entity for use in prediction efforts.

Operation 510 begins by configuring a private data server operating as a modeling engine to receive model instructions (e.g., from a private data server 124 or from central/global server 130) to create a trained actual model 240 from at least some local private data and according to an implementation of at least one machine learning algorithm. The model instructions can be received over a network (e.g., a wireless network, a packet switched network, the Internet, an intranet, a virtual private network, a cellular network, an ad hoc network, a peer-to-peer network, etc.) via one or more protocols. In some embodiments, the model instructions represent a complete, self-contained package. For example, the model instructions can include a compiled implementation of the target machine learning algorithm along with the definition of desired private data features that can be used as a query to generate a training data set. Upon reception of the package, the modeling engine can, if configured to do so, execute training in a secured container. In other embodiments, the model instructions provide a pointer to a locally stored implementation of the machine learning algorithm. Further, the model instructions can include additional information that permit the modeling engine to complete its local training tasks including similarity criteria, similarity score definition, query conversion instructions for selecting private data from a local database, a pre-trained model as a base-line, or other information. For example, if a researcher is interested in determining if patients with a particular tumor mutation, say a single nucleotide polymorphism (SNP), respond to a specific drug, the researcher can construct query criteria based on the mutation and drug and encapsulate the query criteria in the model instructions.

Operation 520 includes the modeling engine creating the trained actual model according to the model instructions and as a function of at least some of the local private data by training the implementation of the machine learning algorithm on the local private data. The modeling engine is able to construct a training data sample based on the private data selection criteria provided within the model instructions. The modeling engine submits the data selection criteria to the local private database, after appropriate formatting to fit the indexing/retrieval system of the local database if necessary. The results set becomes the training set for the target machine learning algorithm. Training the implementation of the target machine learning algorithm on the training set can include adjusting weights of the algorithm, adjusting weights of the inputs to the algorithm, optimizing fitness criteria, executing cross-fold validation, updating a pre-trained model, constraining the system to prevent overfitting, or other actions. The resulting trained actual model includes actual model parameters that can be used to re-instantiate the trained actual model.

Operation 530 includes generating one or more private data distributions from the local private data training sets where the private data distributions represent the training set in aggregate used to create the trained actual model. Depending on the nature of the data (e.g., continuous, discreet, etc.), the private data distributions will vary in their form or nature. In some cases, the data distributions represent one dimension, possibly represented as a histogram, frequency plot, time-varying value, or other one dimensional representation. In other cases, the data distributions represent more than one relevant dimension (e.g., 2D, 3D, etc.). More specifically, higher order dimensional data distributions can include clusters, correlations, contours, density plots, scatter plots, or other types of higher order distributions. The various data distributions can be generated through techniques including creating histograms of values with appropriate binning, creating data plots, fitting curves to data, creating scatter plots, calculating principle components, calculating regressions, or other actions. One should appreciate that generating the distributions can be considered as forming probability density functions or probability mass functions representing the training data set.

Operation 540 includes generating a set of proxy data according to one or more of the private data distributions. The modeling engine leverages the private data distributions as probability distributions from which it is able to generate the proxy data. The modeling engine can generate new proxy data samples by randomly generating new data according to the probability distributions. The modeling engine can compare each sample to where it falls within each of the relevant probability distributions to ensure the sample adheres to the nature of the actual data. Operation 540 can be conducted multiple times or iterated to ensure that the proxy data, in aggregate, generates the proper shapes in the same distribution space. The proxy data could include the same number of samples as the provided data training set; however, it is also possible the proxy data has more or less numbers of samples. Each sample of the proxy data can be compared to samples from the training data to identify if proxy samples are too similar to original actual samples. If similar or if a proxy sample is the same as an actual sample, the proxy sample can be discarded to ensure privacy is maintained. Generation of the proxy data set can be accomplished using a Monte Carlo simulation that is run based on the distributions of the actual data, wherein a seed may be available to generate proxy data in a deterministic manner.

Operation 550 continues with the modeling engine creating a trained proxy model from the proxy data by training the same type or implementation of machine learning algorithm on the proxy data. Of specific note, preferably, the trained proxy model is created from the same implementation of the machine learning algorithm used to create the trained actual model to ensure that the two models can be compared accurately. The modeling engine ensures that the trained proxy model is trained according to the model instructions in a sufficiently similar manner as the trained actual model. The trained proxy model, once finalized, has proxy model parameters that represent the trained proxy model and the proxy data. Even though the trained proxy model and the trained actual model are typically based on the exact same implementation of a machine learning algorithm, their resulting parameter values (e.g., weights, kernels, etc.) could be different.

At operation 560, the modeling engine calculates a model similarity score as a function of the proxy model parameters and actual model parameters. As discussed above, the parameters can be compared pairwise considering that each model is built from the same implementation of the machine learning algorithm and considering that the proxy data has similar features as the private data. In addition to using the proxy and actual model parameters, the modeling engine can also use other factors available in calculating the similarity score. Example additional factors can include accuracies of the model, cross fold validation, accuracy gain, sensitivities, specificities, distributions of the pairwise comparisons (e.g., average value, distributions about zero, etc.). In some embodiments, the actual private data training set can be used to cross-validate the proxy model. If the accuracy of the predictions from the trained proxy model on the actual private data training set is sufficiently high (e.g., within 10%, 5%, 1%, or closer), then the trained proxy model could be considered similar to the trained actual model. Further, if the similarity score fails to satisfy similarity criteria (e.g., falls below a threshold, etc.), then the modeling engine can repeat operations 540 through 560.

Under the condition that the similarity score satisfies similarity criteria, the modeling engine can proceed to operation 570. Operation 570 includes transmitting the set of proxy data, possibly along with other information, over the network to at least one non-private computing device. The non-private computing device could be a centralized hub that aggregates proxy data from private servers or peer hubs or a combination of both. The proxy data can be transmitted over the network as a file (e.g., HDF5), serialized in a mark-up language (e.g., XML, YAML, JSON, etc.), a zip archive, or other format. Additional information beyond the proxy data can also be sent to the remote computing device, a global modeling engine or peer machine for example, including the actual model parameters, proxy model parameters, data distributions, similarity score(s), or other information. Providing the model parameters enables the remote computing device to re-instantiate the trained models and conduct localized validation of the work performed by the private data server's modeling engine. One should note that the actual private data is not transmitted thereby respecting privacy.

Operation 580, performed by a global modeling engine or a peer private data machine, includes aggregating two or more proxy data sets from different private data servers. The aggregate proxy data sets (global proxy sets) are combined based on a given machine learning task and are generated according to the originally requested model instructions. Although each set of proxy data will likely be generated from different private data distributions, it should be appreciated that the corresponding private data training sets are constructed according to the same selection criteria. For example, a researcher might wish to build a prediction model on how well smokers respond to a lung cancer treatment. The research will request models to be built at many private hospitals where each hospital has its own private data. Each hospital receives the same data selection criteria; patients who are smokers, given the treatment, and their associated known outcome. Each hospital's local private data servers, via their modeling engines, constructs their own proxy data using training actual data as a foundation and based on the same data selection criteria. The global modeling engine then aggregates the individual proxy data sets together to create a global training data set. Operation 590 includes the global modeling engine train a global model on the aggregated sets of proxy data. The global model integrates the knowledge gained from each entity's private data. In some embodiments, the global modeling engine can create the trained global model by accumulating sets of actual model parameters and combining them into a single trained model. Such an approach is considered feasible for simplistic, linear algorithms, a linear SVM, for example. However, in more complex embodiments, say neural networks, using proxy data sets is considered superior due to the retention of the potential knowledge in proxy data sets that might be lost through mathematically combining (e.g., adding, averaging, etc.) individual parameters together.

In other embodiments, the global modeling engine also transmits the trained global model back to one or more of the private data servers. The private data servers can then leverage the global trained model to conduct local prediction studies in support of local clinical decision making workflows. In addition, the private data servers can also use the global model as a foundation for continued online learning. Thus, the global model becomes a basis for continued machine learning as new private data becomes available. As new data becomes available, method 500 can be repeated to improve the global modeling engine.

Machine learning systems may receive multiple inputs (e.g., private data), and through the machine learning process, may identify subsets of inputs that are the most important. Thus, it is contemplated that a given hospital may not collect exactly the same type of private data as other hospitals. Thus, the model instructions may be different for different hospitals or sites. However, by identifying which parameters are most predictive using the machine learning systems as described herein, data sets having in common these key predictive parameters may be combined. In other embodiments, model instructions may be modified, e.g., limited to include key predictive features, and used to regenerate proxy data, proxy data distributions, and other types of learned information. This regenerated information can then be sent to the global model server, where it is aggregated.

In other embodiments, a first hospital may collect or filter data in a different manner than a second hospital. Accordingly, there may be different normalizations of data needed before data sets can be combined.

In other embodiments, a researcher may want to perform different analyses on a particular set of private data. For example, a first set of model instructions may indicate that a Gaussian distribution is to be used to build a model. A second set of model instructions may indicate that a Poisson distribution is to be used to build a model. The results can be compared, and the most predictive model selected. The results can also be compared to assess the reproducibility of a given machine learning model.

In still other embodiments, a first set of model instructions may be used to study a particular type of cancer, e.g., to create a breast cancer classifier. The model instructions may then be modified (e.g., additional instructions added, instructions specific to breast cancer removed, and instructions specific to prostate cancer added) and the model instructions then used in a different cancer cohort, e.g., a prostate cancer cohort. Accordingly, it is specifically contemplated that a first set of model instructions for a first type of cancer may be extrapolated to another type of cancer with some modifications. Accordingly, novel relationships between different types of cancers and their treatment can be detected based upon the techniques disclosed herein. For example, a correlation may exist between a first type of cancer and a second type of cancer, such that treating the first type of cancer is predictive of a successful treatment in the second type of cancer.

Figure 6:
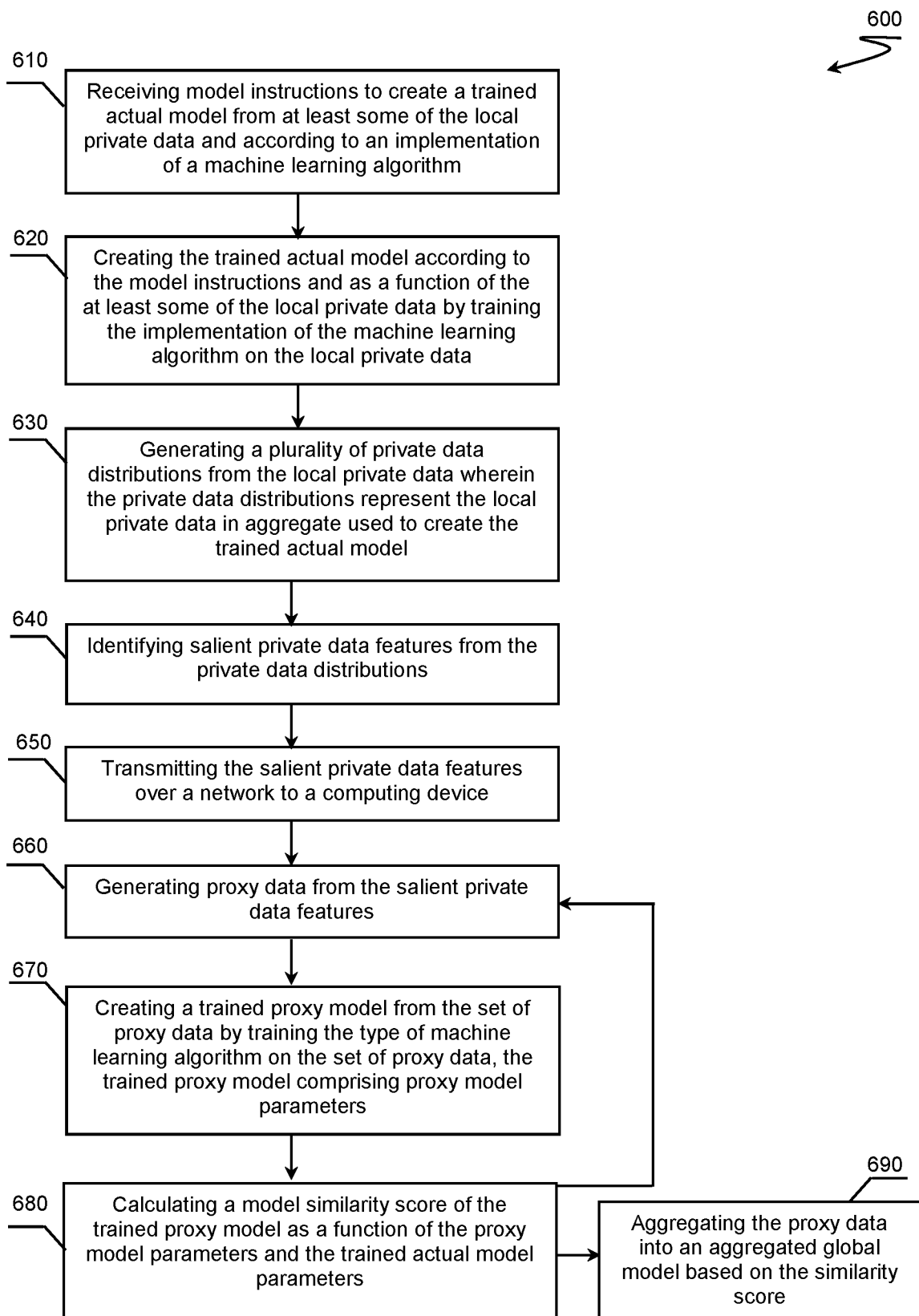
FIG. 6 is an operational flowchart showing an example method of distributed, online machine learning where private data servers transmit salient features of aggregated private data to a non-private computing devices, which in turn creates proxy data for integrating into a trained global model, according to the embodiments presented herein.

FIG. 6 presents computer implemented method 600 representing an alternative, distributed, online machine learning method relative to method 500. Operations 610, 620, and 630 taken by a modeling engine in a private data server are the same as operations 510, 520, and 530 taken by the modeling engine. Method 600 substantially departs from method 500 at operation 640, while initially still focused on the activity of the modeling engine deployed within an entity's private data server. Method 600 seeks to permit remote, non-private computing devices to create global models from the data distributions representative of the local private data from private entities.

Operation 640 includes the modeling engine identifying one or more salient private data features from the local private data distributions. The salient private data features can be considered the data necessary to model the data distributions or to instantiate the distributions in memory of the non-private computing device. Depending on the nature of the distributions, the salient private data features can include one or more of the following: number of samples, principle components, mean, mode, median, type of distribution (e.g., Gaussian, Poisson, decay, etc.), distribution type parameters, histogram binning, moments, correlations, or other features. Further, the salient private data features can, and preferably, include the parameters of the trained actual model that is trained on the actual private data. The actual model parameters are used in the following steps. The salient private data features can be packaged for transmission, according to a markup language (e.g., XML, YAML, JSON, etc.) or any other suitable format.

Operation 650 focuses on the modeling engine transmitting the salient private data features over a network to a remote computing device. In typical embodiments, the salient private data features are transmitted to a global modeling engine that aggregates such salient features from many private entities. Transmission of the features can be based on one or more networking protocols including HTTP, HTTPS, UDP, TCP, FTP, web services (e.g., REST, WSDL, SOAP, etc.), or other protocols.

Operation 660 shifts focus from the modeling engine in an entity's private data server to the non-private computing device's global modeling engine (see FIG. 1, global modeling engine 136). The global modeling engine receives the salient private data features and locally re-instantiates the private data distributions in memory. As discussed previously with respect to operation 540, the global modeling engine generates proxy data from the salient private data features, for example, by using the re-instantiated private data distributions as probability distributions to generate new, synthetic sample data. The generated proxy data is not required to have the same number of samples as the original, actual data. Rather, the proxy data merely needs a sufficient number of samples of sufficient quality to create a similar trained model to the trained model created from the actual private data.

In some embodiments, the salient private data features could include proxy data, from which the data distributions can be re-derived. However, in the example of method 600, it is considered advantageous for each private data server to generate its own salient features. One reason for this approach is because each private data server's modeling engine can operate in parallel and in a distributed fashion rather than requiring the global modeling engine to perform all the work on the proxy data sets in a centralized, serial fashion. Thus, the overall system has improved throughput. Still, in some scenarios where proxy data is sparse, it is reasonable for the global modeling engine to receive the proxy data because the sparse proxy data could be more compact to send than the package salient private data features. The conditions or requirements for deciding whether to send the proxy data can be packaged in the original model instructions.

In operation 670, similar to operation 550 of FIG. 5, the global modeling engine creates a trained proxy model from the set of proxy data by training the same type of or implementation of the machine learning algorithm used to create the trained actual model. In this case, the proxy data becomes the training data set. Once the trained proxy model has completed training, it has a set of proxy model parameters that define the trained model. As discussed previously, the proxy model parameters can be used to re-instantiate the trained proxy model in the memory of a target computing device (e.g., a private data server).

Operation 680, similar to operation 560 of FIG. 6, includes the global modeling engine calculating a model similarity score of the trained proxy model relative to the trained actual model(s) as a function of the proxy model parameters and the actual proxy model parameters. The actual proxy model parameters can be obtained along with the salient private data features as discussed with respect to operation 640 or could be obtained upon sending a request to the proxy data's modeling engine. Should the model similarity score fail to satisfy similarity requirements, then the global modeling engine can repeat operations 660 through 680 until a satisfactorily similar trained proxy model is generated.

Operation 690 includes the global modeling engine, upon determining that the trained proxy model satisfies the similarity requirements, aggregating the proxy data into an aggregated global model. The proxy data is aggregated with other proxy data from other private data servers to create the aggregated model. It should be appreciated that this approach can be performed in an online learning manner where the aggregated global model is continually updated with new proxy data as time passes.

In yet more interesting embodiments, generated global models can be transmitted to the modeling engine within the private data servers to be used for prediction purposes. Further, the global models can be leveraged as a foundation from which the private data servers build trained actual models. This approach is considered advantageous because private data servers lacking sufficient quantity of data samples will be able to still add to their contribution to the discovery of knowledge.

The disclosed approach of distributed, online machine learning can leverage numerous techniques for validating trained models. One approach includes a first private data server sending its trained actual model to other private data servers. The other private data servers can then validate the trained actual model on their own local data and send the results back to the first private data server. Additionally, a global modeling engine could also execute one or more cross-fold validation steps on the trained actual models using the global collection of aggregated proxy data. The reverse is also true. The global modeling engine can send the global mode to one or more private data servers to have the global model validated on each private data server's local data. One should appreciate that the validation of the various models is to be performed on data sets selected according to the same data selection requirements to ensure a proper analysis.

Yet another interesting aspect of the disclosed inventive subject matter is that the various trained models can be managed over time as data is accumulated. Each model can be considered a member of overarching distributed research tasks having specific data requirements. Thus, each model can be bound with task identifiers (e.g., name, goal, GUID, UUID, etc.) that allow the various modeling engines to manage their models on a task basis. In addition to creating a de novo model, the modeling engines can retain each trained model or proxy data over time. As new data becomes visible to the private data server, the modeling engine can detect the data, possibly via a task-specific listener and then integrate relevant new data in the actual trained data. Further, the relevant data distributions can be updated accordingly. In some cases, a brand new proxy data set is generated, while in the cases only new samples are generated which can be added to previously generated proxy data. Thus, the inventive subject matter is considered to include establishment of time varying model management rules by which modeling engines govern models associated with a research task. Example rules include reporting out updates, monitoring model parameters over time, inventorying existing models or research tasks, generating alerts as models or data change, recovering lost models from a global model server (e.g., a global modeling hub, global modeling engine, etc.), logging modeling or research tasks, securing the models, or other management functions.

The disclosed ecosystem/system provides a distributed, online learning across many computing devices where each computing device (e.g., global modeling engines, private data servers, etc.) has one or more modeling engines. The modeling engines are configurable to manage many modeling tasks. Thus, the number of active models could number in the hundreds, thousands, or even more than one million models. Therefore, the inventive subject matter is also considered to include management apparatus or methods of the large number of model objects in the distributed system. For example, each modeling task can be assigned one or more identifiers, or other metadata, for management by the system. More specifically, identifiers can include a unique model identifier, a task identifier that is shared among models belonging to the same task, a model owner identifier, time stamps, version numbers, an entity or private data server identifier, geostamps, or other types of IDs. Further, the global modeling engine can be configured to present a dashboard to a researcher that compiles and presents the status of each project. The dashboard can be configured to drill down to specific models and their current state (e.g., NULL, instantiated, training, trained, updated, deleted, etc.).

There are numerous possible uses for the disclosed technologies. Although the subject matter of the disclosure has primarily focused on training models with respect to treatments and outcomes of patients who have mutations, there are also other possible uses. One primary use is that the resulting locally trained actual models or global models can be the foundation of a clinical trial recommendation system. Consider a case where there are numerous trained models, actual local models or global models, which have been trained on treatment and outcome data for various patients and drugs, including drugs that are in clinical trials. As new patients are diagnosed with various diseases (e.g., cancer, etc.), the modeling engine located at the patient's care facility can submit the patient's data (e.g., WGS, WES, genome diff objects, symptoms, demographics, etc.) to available relevant trained actual models, to trained proxy models or trained global models. The trained models will yield a prediction of whether the patient would respond to particular treatments on which the models are originally trained. If the models predict that a patient would respond to treatments that are currently under trial, then the system can present a ranked listing of possible clinical trials for which the patient might be a candidate; ranked according to prediction confidence for example. When a possible patient-trial match is detected, the modeling engines can generate an alert or other notification where the notification is routed to one or more patient care stakeholders. Still further, as the patient experiences treatment, their data can be fed back into the trained actual, proxy and global models to ensure the trained models are updated through additional training.

Still another interesting aspect of the inventive subject includes creating the opportunity for discovery of outlier events. Reconsider the scenario where a new patient's data enters the system and the modeling engines in the system makes predications regarding the patient's possible treatment outcomes. Further, consider that the patient is predicted to be a non-responder to a specific treatment, possibly based on a specific genomic variant. However, the patient is later found to be a responder. When one or more modeling engines detect a significant difference between a prediction and an actual outcome, the modeling engines can generate a notification for the researcher who owns or manages the trained models. Detection of such an outlier provides several insights. For example, the outlier might indicate a weakness in one or more of the trained models. Additionally, the outlier might be a true outlier that should be studied further to determine what differences (e.g., other genomic differences, etc.) in the outlier relative to the training data set causes the data to be an outlier. Automated outlier detection or discovery provides possible avenues of further research.

Beyond health care, the disclosed techniques can also be leveraged for AI research, possibly with respect to computer game development. In such cases, a computer game console (e.g., PS4, X-Box, PC, etc.) can be configured with a game-specific modeling engine as disclosed above. As individual players play the game, the modeling engine observes the players interaction with a given scenario (i.e., collects input) and detects the success of the player (i.e., outcomes) to generate training data for a local trained actual model. Using the techniques described above, proxy data can then be generated from many players to create a global trained model. The global trained model can then be foundation for the game's AI. The game's AI can use the global trained model to predict a new player's possible next move(s) to anticipate what will happen next. The game can then shift tactics or strategies accordingly to create more challenging game play. Other markets beyond health care and gaming that can leverage the disclosed techniques including insurance policy analysis, consumer transaction analysis, commuter traffic analysis, or other types of analyses having large quantities of high quality training data that is required to remain secure.

Yet another possible area where the disclosed inventive subject matter would be useful includes learning from private image collections. Consider an example where there are multiple, distributed caches of private images; on many person's individual home computers for example. The disclosed techniques would allow a researcher or a data analysts to study information within the private image collections without requiring access to the specific images. Such a feat can be achieved by, assuming the owner's permission is granted, installing a modeling engine on each person's computer. The modeling engine can receive local training data in the form of original images along with other training information (e.g., annotations, classifications, scene descriptions, locations, time, settings, camera orientations, etc.) as defined according to the modeling instructions. The modeling engine can then create local trained actual models from the original images and training information. Proxy data can be generated through constructing similar images, possibly based on eigenvectors of the trained actual model.

For example, it should be appreciated that the private image collections could reside on a computer or data storage facility associated with or in a number of different physician's offices, medical imaging facilities, or clinical/pathology laboratories, typically in geographically distinct locations (e.g., different communities, cities, ZIP codes, states, etc.). In such case, the image collections would comprise of various scans (e.g., PET, SPECT, CT, fMRI, etc.) that would be associated with specific patients and their respective diagnostic and treatment histories. Or images could comprise tissue sections (typically stained with a dye, fluorophore, or otherwise optically detectable entity) or immuno-histochemically treated sections associated with relevant patient information. Yet further contemplated images will include sonographic images (e.g., 2D, 3D, doppler) or videos, or angiographic images or videos, again associated with relevant patient information.

As should be readily apparent, contemplated distributed learning systems as discussed herein will provide numerous benefits. For example, large scale analysis of patterns (e.g., image acquisition of an entire tissue section instead of analysis of a single visual field in a microscope) can be subjected to the distributed learning system to so allow for significantly larger datasets to be processed in a manner that a human would not be able to do. Moreover, parameters that are often only perceived by a clinician as intuitive cues can be delineated by a distributed learning system as a large number of corresponding images or videos are available for the learning process. In addition, it should be noted that the so learned information can be shared across a large network of subscribers that are informationally coupled to the distributed learning system without compromising patient identity and condition.

Alternatively, rather than attempting to generate similar images from a human perspective, the modeling engine can generate synthetic images having computer-understandable features (e.g., descriptors, key points, etc.), possibly using genetic algorithms. Descriptors may be single valued or multivalued and may include similarity scores (a histogram descriptor). Assuming for the sake of discussion, the modeling engine is trained based on SIFT descriptors (i.e., see U.S. Pat. No. 6,711,293 to Lowe titled "Method and Apparatus for Identifying Scale Invariant Features in an Image and Use of Same for Locating an Object in an Image", filed Mar. 6, 2000) and classification information provided by the image owners. Proxy images can be generated using random overlapping, semi-transparent polygons. A genetic algorithm can vary the parameters of the polygons and then use the SIFT descriptors of the proxy images relative to the SIFT descriptors of the original image as a measure of fitness. When the proxy image's SIFT descriptors are sufficiently similar (e.g., similar distributions, similar values, similar number of descriptors, etc.), the proxy image is complete. One should note that this approach is considered advantageous because the resulting proxy image would be machine understandable, but would not be human understandable, which allows the remote non-private computing devices to be able to learn from the proxy images. In other embodiments, parameters for a learned model may be provided to a system and the system may generate corresponding descriptors.

The methods presented herein are not limited to the specific order of operations that are presented. One of skill in the art would realize that many such sequences and variations are possible.

Many different embodiments are contemplated herein, including the entire system 100, the private data server, the peer data server and the global modeling engine, etc. Accordingly, claims are presented in Table 1 that encompass at least some of the aforementioned embodiments, including:

TABLE 1

1. A computer implemented method of generating proxy data using a private data server configured to access local private data, and including at least one modeling engine configured to:
   create, from the private data, a trained actual model using a machine learning algorithm;
   generate a plurality of private data distributions from at least some of the local private data, wherein the private data distributions represent the local private data in aggregate;
   generate a set of proxy data based on the plurality of private data distributions; and
   create, from the set of proxy data, a trained proxy model using the machine learning algorithm.
2. The method of claim 1, wherein the machine learning algorithm used to create the trained proxy model is the same machine learning algorithm used to create the trained actual model.
3. The method of claim 1, wherein the private data server receives model instructions from a global server to create the trained actual model from at least some of the local private data.
4. The method of claim 3, wherein the trained actual model is created based on the model instructions and at least some of the local private data, and wherein the machine learning algorithm is trained on the local private data.
5. The method of claim 1, wherein the trained proxy model produces proxy model parameters and wherein the trained actual model produces trained actual model parameters.
6. The method of claim 5, wherein the private data server is configured to calculate a model similarity score as a function of the proxy model parameters and the trained actual model parameters.
7. The method of claim 6, wherein the private data server is configured to transmit the set of proxy data, over a network, to at least one non-private computing device as a function of the model similarity score.
8. The method of claim 1, wherein the local private data includes patient-specific data.
9. The method of claim 1, wherein the local private data includes at least one of the following types of data: genomic data, whole genome sequence data, whole exosome sequence data, proteomic data, proteomic pathway data, k-mer data, neoepitope data, RNA data, allergy information, encounter data, treatment data, outcome data, appointment data, order data, billing code data, diagnosis code data, results data, treatment response data, tumor response data, demographic data, medication data, vital sign data, payor data, drug study data, drug response data, longitudinal study data, biometric data, financial data, proprietary data, electronic medical record data, research data, human capital data, performance data, analysis results data, or event data.
10. The method of claim 1, wherein the modeling engine is further configured to update the trained actual model on new local private data.
11. The method of claim 3, wherein the model instructions include instructions to create the trained actual model from a base-line model created external to the private data server.
12. The method of claim 11, wherein the base-line model comprises a global trained model.
13. The method of claim 6, wherein the similarity score is determined based on a cross validation of the trained proxy model.
14. The method of claim 13, wherein the cross validation includes one or more of:
    (1) an internal cross validation on a portion of the proxy data;
    (2) an internal cross validation of a portion of the local private data; or
    (3) an external cross validation by a different one of the plurality of private data servers on its local private data.
15. The method of claim 6, wherein the similarity score comprises one of:
    (1) a difference between an accuracy measure of the proxy model and an accuracy measure of the trained actual model; or
    (2) a metric distance calculated using the trained actual model parameters and the proxy model parameters.
16. The method of claim 7, wherein the proxy data is transmitted when the function of the model similarity score satisfies at least one transmission criterion.
17. The method of claim 16, wherein the at least one transmission criterion includes at least one of the following conditions relating to the similarity score: a threshold condition, a multi-valued condition, a change in value condition, a trend condition, a human command condition, an external request condition, and a time condition.

TABLE 1-continued

18. The method of claim 1, wherein a local storage system that stores the private data includes at least one of the following: a local database, a BAM server, a SAM server, a GAR server, a BAMBAM server, and a clinical operating system server.
19. The method of claim 1, wherein a distribution of the plurality of private data distributions adheres to at least one of the following types of distributions: a Gaussian distribution, a Poisson distribute, a Bernoulli distribution, a Rademacher distribution, a discrete distribution, a binomial distribution, a zeta distribution, a Gamma distribution, a beta distribution, and a histogram distribution.
20. The method of claim 1, wherein the private data distributions are based on eigenvalues derived from the trained actual model parameters and the private local data.
21. The method of claim 1, wherein the set of proxy data includes combinations of eigenvectors derived from the trained actual model parameters and the local private data.
22. The method of claim 21, wherein the proxy data comprises linear combinations of the eigenvectors.
23. The method of claim 22, wherein the eigenvectors include at least one of the following: an eigenpatient, an eigenprofile, an eigendrug, an eigenhealth record, an eigengenome, an eigenproteome, an eigenRNA profile, and an eigenpathway.
24. The method of claim 1, wherein the trained actual model is based on an implementation of at least one of the following types of machine learning algorithms: a classification algorithm, a neural network algorithm, a regression algorithm, a decision tree algorithm, a clustering algorithm, a genetic algorithm, a supervised learning algorithm, a semi-supervised learning algorithm, an unsupervised learning algorithm, or a deep learning algorithm.
25. The method of claim 1, wherein the trained actual model is based on an implementation of at least one of the following types of machine learning algorithms: a support vector machine, a nearest neighbor algorithm, a random forest, a ridge regression, a Lasso algorithm, a k-means clustering algorithm, a spectral clustering algorithm, a mean shift clustering algorithm, a non-negative matrix factorization algorithm, an elastic net algorithm, a Bayesian classifier algorithm, a RANSAC algorithm, and an orthogonal matching pursuit algorithm.
26. A computer implemented method of generating proxy data in a distributed machine learning system comprising a plurality of private data servers and a global model server including at least one global modeling engine configured to:
    generate model instructions based on a query;
    transmit the model instructions to the plurality of private data servers;
    receive a set of proxy data from each server of the plurality of private data servers;
    aggregate the sets of proxy data into a global proxy data; and
    train a global aggregate model using the global proxy data.
27. The method of claim 26, further comprising:
    generating a first set of model instructions based on the query, and transmitting the first set of model instructions to a first private data server;
    generating a second set of model instructions based on the query, wherein the second set of instructions are different from the first set of model instructions, and transmitting the second set of model instructions to a second data server;
    receiving a first set of proxy data from the first private data server, and receiving a second set of proxy data from the second private data server;
    aggregating the first set of proxy data and the second set of proxy data into the global proxy data.
28. The method of claim 26, further comprising:
    receiving from a private data server, metadata indicating types of private data stored on the private data server;
    generating model instructions based on the metadata.
29. The method of claim 26, further comprising providing updated modeling instructions to the plurality of private data servers, based upon the global aggregate model.
30. The method of claim 26, wherein the global trained model is trained, at least in part, on sets of proxy data from at least two of the plurality of private data servers.
31. A computer implemented method of generating proxy data using a private data server configured to access local private data, and including at least one modeling engine configured to:
    receive from a peer private data server, a set of peer proxy data based on peer private data stored on the peer private data server;
    create, from local private data stored on the private data server, a trained actual model using a machine learning algorithm;
    generate a plurality of private data distributions from at least some of the local private data;
    generate a set of proxy data based on the plurality of private data distributions;
    combine the set of peer proxy data with the set of proxy data to form a set of aggregate proxy data;
    create, from the set of aggregate proxy data, a trained proxy model using the machine learning algorithm on the private data server.
32. The method of claim 31, wherein the private data distributions represent the local private data in aggregate.
33. The method of claim 31 comprising transmitting the aggregate proxy data to a global modeling engine.
34. The method of claim 31, wherein the peer private data server lacks authorization to access the local private data on the private data server.
35. A computer implemented method of distributed machine learning comprising:
    receiving, by a private data server, model instructions to create a trained actual model from at least some of local private data local to the private data server and according to an implementation of a machine learning algorithm;

TABLE 1-continued creating, by a machine learning engine, the trained actual model according to the model instructions and as a function of the at least some of the local private data by training the implementation of the machine learning algorithm on the local private data, the trained actual model comprising trained actual model parameters;
generating, by the machine learning engine, a plurality of private data distributions from the local private data where the private data distributions represent the local private data in aggregate used to create the trained actual model;
identifying, by the machine learning engine, salient private data features from the private data distribution wherein the salient private data features allow for replication of the plurality of proxy data distributions; and
transmitting, by the machine learning engine, the salient private data features over a network to a non-private computing device.
36. The method of claim 35, wherein the salient private data features includes a set of proxy data.
37. The method of claim 35, further comprising generating a set of proxy data according to at least one of the following: the plurality of private data distributions, and the salient private data features.
38. The method of claim 37, further comprising creating a trained proxy model from the set of proxy data by training the type of the implementation of the machine learning algorithm on the set of proxy data, the trained proxy model comprising proxy model parameters.
39. The method of claim 38, further comprising calculating a model similarity score of the trained proxy model as a function of the proxy model parameters and the trained actual model parameters.
40. The method of claim 39, further comprising aggregating the set of proxy data into an aggregated global model based on the model similarity score.
41. A distributed machine learning system comprising:
a storage device storing local private data;
a plurality of private data servers, wherein the plurality of private data servers are communicatively coupled via a network, each private data server configured to access the local private data, wherein each private data server comprises one or more processors and at least one modeling engine configured to:
create, from the private data, a trained actual model using a machine learning algorithm;
generate a plurality of private data distributions from at least some of the local private data, wherein the private data distributions represent the local private data in aggregate;
generate a set of proxy data based on the plurality of private data distributions; and
create, from the set of proxy data, a trained proxy model using the machine learning algorithm.
42. The system of claim 41, wherein the machine learning algorithm used to create the trained proxy model is the same machine learning algorithm used to create the trained actual model.
43. The system of claim 41, wherein the private data server receives model instructions via a network interface from a global server to create the trained actual model from at least some of the local private data.
44. The system of claim 43, wherein the trained actual model is created based on the model instructions and based on at least some of the local private data, and wherein the machine learning algorithm is trained on the local private data.
45. The system of claim 41, wherein the trained proxy model produces proxy model parameters and wherein the trained actual model produces trained actual model parameters.
46. The system of claim 45, wherein the private data server is configured to calculate a model similarity score as a function of the proxy model parameters and the trained actual model parameters.
47. The system of claim 46, wherein the private data server is configured to transmit via a network interface the set of proxy data, over a network, to at least one non-private computing device as a function of the model similarity score.
48. The system of claim 41, wherein the modeling engine is further configured to update the trained actual model on new local private data.
49. The system of claim 41, wherein model instructions include instructions to create the trained actual model from a base-line model created external to the private data server.
50. The system of claim 49, wherein the base-line model comprises a global trained model.
51. The system of claim 47, wherein the proxy data is transmitted when a model similarity score satisfies at least one transmission criterion.
52. The system of claim 51, wherein the at least one transmission criterion includes at least one of the following conditions relating to the similarity score: a threshold condition, a multi-valued condition, a change in value condition, a trend condition, a human command condition, an external request condition, and a time condition.
53. The system of claim 41, wherein a local storage system that stores the private local data includes at least one of the following: a local database, a BAM server, a SAM server, a GAR server, a BAMBAM server, or a clinical operating system server.
54. The system of claim 41, wherein the trained actual model is based on an implementation of at least one of the following types of machine learning algorithms: a classification algorithm, a neural network algorithm, a regression algorithm, a decision tree algorithm, a clustering algorithm, a genetic algorithm, a supervised learning algorithm, a semi-supervised learning algorithm, an unsupervised learning algorithm, or a deep learning algorithm, a support vector machine, a nearest neighbor algorithm, a random forest, a ridge regression, a Lasso algorithm, a k-means clustering algorithm, a spectral clustering algorithm, a mean shift clustering algorithm, a non-negative matrix factorization algorithm, an elastic net algorithm, a Bayesian classifier algorithm, a RANSAC algorithm, or an orthogonal matching pursuit algorithm.

TABLE 1-continued

55. A global modeling server, in a distributed machine learning system comprising a plurality of private data servers that are communicatively coupled via a network, wherein the global modeling server includes one or more processors and at least one global modeling engine configured to:
generate model instructions based on a query;
transmit the model instructions via a network interface to a plurality of private data servers;
receive a set of proxy data via the network interface from the plurality of private data servers;
aggregate the sets of proxy data into a global proxy data; and
train a global aggregate model using the global proxy data.
56. The server of claim 55, wherein the global modeling engine is further configured to:
generate a first set of model instructions based on the query, and transmitting via a network interface the first set of model instructions to a first private data server;
generate a second set of model instructions based on the query, wherein the second set of instructions are different from the first set of model instructions, and transmitting via the network interface the second set of model instructions to a second data server;
receive a first set of proxy data from the first private data server, and receiving via the network interface a second set of proxy data from the second private data server; and
aggregate the first set of proxy data and the second set of proxy data into the global proxy data.
57. The server of claim 55, wherein the global modeling engine is further configured to:
receive via the network interface metadata from a private data server indicating types of private data stored on the private data server; and
generate model instructions based on the metadata.
58. The server of claim 55, wherein the global modeling engine is further configured to:
provide updated modeling instructions to the plurality of private data servers via the network interface, based upon the global aggregate model.
59. The server of claim 55, wherein the global trained model is trained, at least in part, on sets of proxy data from at least two of the plurality of private data servers.
60. A private data server, in a distributed machine learning system comprising a plurality of private data servers, communicatively coupled through a network, and a global model server, wherein the private data server includes one or more processors and at least one modeling engine and is configured to:
receive from a peer private data server via a network interface, a set of peer proxy data based on peer private data stored on the peer private data server;
create, from local private data stored on the private data server, a trained actual model using a machine learning algorithm;
generate a plurality of private data distributions from at least some of the local private data;
generate a set of proxy data based on the plurality of private data distributions;
combine the set of peer proxy data with the set of proxy data to form a set of aggregate proxy data;
create, from the set of aggregate proxy data, a trained proxy model using the machine learning algorithm on the private data server.
61. The private data server of claim 60, wherein the private data distributions represent the local private data in aggregate.
62. The private data server of claim 60, wherein the private data server is further configured to transmit the aggregate proxy data via a network interface to a global modeling engine.
63. The private data server of claim 60, wherein the peer private data server lacks authorization to access the local private data on the private data server.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification or claims refer to at least one of something selected from the group consisting of A, B, C . . . and N, the text should be interpreted as requiring only one element from the group, not A plus N, or B plus N, etc.

What is claimed is:
1. A distributed machine learning system comprising:
a plurality of private data servers,
wherein each private data server of the plurality of private data servers has access to local private data and has at least one modeling engine,
wherein the plurality of private data servers is communicatively coupled, via a network, to at least one non-private computing device,
wherein, for each private data server of the plurality of private data servers, the local private data includes restricted features to which the at least one non-private computing device does not have authorization to access, and
wherein each private data server of the plurality of private data servers, upon execution by at least one processor of software instructions stored in a non-transitory computer readable memory, causes its at least one modeling engine to:
receive model instructions to create a trained actual model from at least some of the local private data and according to an implementation of a machine learning algorithm;
create the trained actual model according to the model instructions and as a function of the at least some of the local private data by training the implementation of the machine learning algorithm on the local private data, the trained actual model comprising trained actual model parameters;

generate a plurality of private data statistical distributions from the local private data where the plurality of private data statistical distributions represents the local private data in aggregate used to create the trained actual model and does not include individual elements of the local private data;

generate a set of proxy data according to the plurality of private data statistical distributions;

create a trained proxy model from the set of proxy data by training another implementation of the machine learning algorithm on the set of proxy data, wherein the trained proxy model comprises proxy model parameters;

calculate a model similarity score based on the proxy model parameters and the trained actual model parameters;

determine whether the model similarity score satisfies at least one transmission criterion, wherein the at least one transmission criterion includes at least one of the following conditions relating to the model similarity score: a threshold condition, a multi-valued condition, a change in value condition, a trend condition, a human command condition, an external request condition, and a time condition;

in response to a determination that the model similarity score satisfies the at least one transmission criterion, transmit the set of proxy data, the proxy model parameters and the similarity score, over the network, to the at least one non-private computing device; and in response to the determination that the model similarity score does not satisfy the at least one transmission criterion:

receive updated model instructions from the at least one non-private computing device, wherein the at least one non-private computing device is configured to aggregate proxy data received from multiple ones of the plurality of private data servers and update a global model according to the aggregated data, and the updated model instructions include updated parameters according to the updated global model; and generate a second trained actual model according to the updated model instructions received from the at least one non-private computing device based on the aggregated proxy data.

2. The system of claim 1, wherein the local private data comprises local private healthcare data.

3. The system of claim 2, wherein the local private healthcare data includes patient-specific data.

4. The system of claim 1, wherein the local private data includes at least one of the following types of data: genomic data, whole genome sequence data, whole exosome sequence data, proteomic data, proteomic pathway data, k-mer data, neoepitope data, RNA data, allergy information, encounter data, treatment data, outcome data, appointment data, order data, billing code data, diagnosis code data, results data, treatment response data, tumor response data, demographic data, medication data, vital sign data, payor data, drug study data, drug response data, longitudinal study data, biometric data, financial data, proprietary data, electronic medical record data, research data, human capital data, performance data, analysis results data, and event data.

5. The system of claim 1, wherein the network comprises at least one of the following types of networks: a wireless network, a packet switched network, the Internet, an intranet, a virtual private network, a cellular network, an ad hoc network, and a peer-to-peer network.

6. The system of claim 1, wherein the at least one non-private computing device is a different one of the plurality of private data servers lacking authorization to the local private data on which the trained actual model was created.

7. The system of claim 1, wherein the at least one non-private computing device includes a global model server.

8. The system of claim 7, wherein the global model server is configured to aggregate sets of proxy data from at least two of the plurality of private data servers and is configured to train a global model on the sets of proxy data.

9. The system of claim 1, wherein each private data server is communicatively coupled with a local storage system that stores the local private data.

10. The system of claim 9, wherein the local storage system includes at least one of the following: a RAID system, a file server, a network accessible storage device, a storage area network device, a local computer readable memory, a hard disk drive, an optical storage device, a tape drive, a tape library, and a solid state disk.

11. The system of claim 9, wherein the local storage system includes at least one of the following: a local database, a BAM server, a SAM server, a GAR server, BAMBAM server, and a clinical operating system server.

12. The system of claim 1, wherein the model instructions comprise at least one of the following: a local command, a remote command, an executable file, a protocol command, and a selected command.

13. The system of claim 1, wherein, for each statistical distribution of the plurality of private data statistical distributions, the statistical distribution is generated such that the statistical distribution comprises at least one of the following types of statistical distributions: a Gaussian distribution, a Poisson distribution, a Bernoulli distribution, a Rademacher distribution, a discrete distribution, a binomial distribution, a zeta distribution, a Gamma distribution, a beta distribution, and a histogram distribution.

14. The system of claim 1, wherein the plurality of private data statistical distributions are based on eigenvalues derived from the trained actual model parameters and the local private data.

15. The system of claim 1, wherein the set of proxy data includes combinations of eigenvectors derived from the trained actual model parameters and the local private data.

16. The system of claim 15, wherein the set of proxy data comprises linear combinations of the eigenvectors.

17. The system of claim 15, wherein the eigenvectors include at least one of the following: an eigenpatient, an eigenprofile, an eigendrug, an eigenhealth record, an eigengenome, an eigenproteome, an eigenRNA profile, and an eigenpathway.

18. The system of claim 1, wherein the trained actual model is based on an implementation of at least one of the following types of machine learning algorithms: a classification algorithm, a neural network algorithm, a regression algorithm, a decision tree algorithm, a clustering algorithm, a genetic algorithm, a supervised learning algorithm, a semi-supervised learning algorithm, an unsupervised learning algorithm, and a deep learning algorithm.

19. The system of claim 1, wherein the trained actual model is based on an implementation of at least one of the following machine learning algorithms: a support vector machine, a nearest neighbor algorithm, a random forest, a ridge regression, a Lasso algorithm, a k-means clustering algorithm, a spectral clustering algorithm, a mean shift clustering algorithm, a non-negative matrix factorization algorithm, an elastic net algorithm, a Bayesian classifier algorithm, a RANSAC algorithm, and an orthogonal matching pursuit algorithm.

20. The system of claim 1, wherein, for a first private data server of the plurality of private data servers, the model instructions include instructions to create the trained actual model from a baseline model created external to the first private data server.

21. The system of claim 20, wherein the baseline model comprises a global trained actual model.

22. The system of claim 21, wherein the global trained actual model is trained, at least in part, on sets of proxy data from at least two of the plurality of private data servers other than the first private data server.

23. The system of claim 1, wherein the model similarity score is determined based on a cross validation of the trained proxy model.

24. The system of claim 23, wherein the cross validation includes an internal cross validation on a portion of the set of proxy data.

25. The system of claim 23, wherein the cross validation includes an internal cross validation of the local private data.

26. The system of claim 23, wherein the cross validation includes an external cross validation by a different one of the plurality of private data servers on its local private data.

27. The system of claim 1, wherein the model similarity score comprises a difference between an accuracy measure of the trained proxy model and an accuracy measure of the trained actual model.

28. The system of claim 1, wherein the model similarity score comprises a metric distance calculated from the trained actual model parameters and the proxy model parameters.

29. The system of claim 1, wherein the modeling engine is further configured to update the trained actual model on new local private data.

30. A computing-device-implemented method of distributed machine learning, the method comprising:
receiving, by a private data server, model instructions to create a trained actual model from at least some of local private data local to the private data server and according to an implementation of a machine learning algorithm, wherein the local private data includes restricted features;
creating, by a machine learning engine, the trained actual model according to the model instructions and as a function of the at least some of the local private data by training the implementation of the machine learning algorithm on the local private data, wherein the trained actual model comprises trained actual model parameters;
generating, by the machine learning engine, a plurality of private data statistical distributions from the local private data, wherein the plurality of private data statistical distributions represents the local private data in aggregate used to create the trained actual model and does not include individual elements of the local private data;
identifying, by the machine learning engine, salient private data features from the plurality of private data statistical distributions, wherein the salient private data features allow for replication of the plurality of private data statistical distributions;
creating a trained proxy model from a set of proxy data by training another implementation of the machine learning algorithm on the set of proxy data, wherein:
the set of proxy data is associated with the plurality of private data statistical distributions and
the trained proxy model comprises proxy model parameters;
in response to a determination that a model similarity score of the trained proxy model satisfies at least one transmission criterion, transmitting, by the machine learning engine, the salient private data features, the proxy model parameters and the model similarity score over a network to a non-private computing device; and
in response to the determination that the model similarity score does not satisfy the at least one transmission criterion:
receiving updated model instructions from the at least one non-private computing device, wherein the non-private computing device is configured to aggregate proxy data received from multiple ones of the plurality of private data servers and update a global model according to the aggregated data, and the updated model instructions include updated parameters according to the updated global model; and
generating a second trained actual model according to the updated model instructions received from the non-private computing device based on the aggregated proxy data;
wherein the model similarity score is based on the proxy model parameters and the trained actual model parameters,
wherein the non-private computing device is not authorized to access the restricted features of the local private data, and
wherein the salient private data features exclude the restricted features.

31. The method of claim 30, wherein the salient private data features includes a set of proxy data.

32. The method of claim 30, further comprising generating the set of proxy data according to at least one of the following: the plurality of private data statistical distributions and the salient private data features.

33. The method of claim 30, further comprising calculating the model similarity score of the trained proxy model as a function of the proxy model parameters and the trained actual model parameters.

34. The method of claim 33, further comprising aggregating the set of proxy data into an aggregated global model based on the model similarity score.

35. A computer-implemented method of generating proxy data, the method comprising:
creating, at a private data server, from local private data accessible to the private data server, a trained actual model using a machine learning algorithm, wherein:
the trained actual model comprises trained actual model parameters;
the local private data includes restricted features that are accessible to the private data server and are inaccessible to at least one system; and
the restricted features include protected health information;
generating, at the private data server, a plurality of private data statistical distributions from at least some of the local private data, wherein the plurality of private data statistical distributions represents the local private data in aggregate and does not include individual elements of the local private data;

generating, at the private data server, a set of proxy data based on the plurality of private data statistical distributions, wherein the restricted features are absent from the set of proxy data;

creating, at the private data server, from the set of proxy data, a trained proxy model using the machine learning algorithm, wherein the trained proxy model comprises proxy model parameters;

calculating, at the private data server, a model similarity score based on the proxy model parameters and the trained actual model parameters;

determining, at the private data server, that the model similarity score satisfies at least one transmission criterion, wherein the at least one transmission criterion includes at least one of the following conditions relating to the model similarity score: a threshold condition, a multi-valued condition, a change in value condition, a trend condition, a human command condition, an external request condition, and a time condition;

in response to the determination that the model similarity score satisfies the at least one transmission criterion, distributing, by the private data server, the trained proxy model, the proxy model parameters and the similarity score to the at least one system that lacks access to the restricted features; and in response to the determination that the model similarity score does not satisfy the at least one transmission criterion:

receive updated model instructions from the at least one non-private computing device, wherein the at least one non-private computing device is configured to aggregate proxy data received from multiple ones of the plurality of private data servers and update a global model according to the aggregated data, and the updated model instructions include updated parameters according to the updated global model; and generate a second trained actual model according to the updated model instructions received from the at least one non-private computing device based on the aggregated proxy data.

* * * * *